(12) United States Patent
Gao et al.

(10) Patent No.: US 9,034,832 B2
(45) Date of Patent: *May 19, 2015

(54) SOLID COMPOSITIONS

(71) Applicant: AbbVie Inc., North Chicago, IL (US)

(72) Inventors: Yi Gao, Vernon Hills, IL (US); Geoff Zhang, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/507,267

(22) Filed: Oct. 6, 2014

(65) Prior Publication Data

US 2015/0025024 A1    Jan. 22, 2015

Related U.S. Application Data

(63) Continuation-in-part of application No. 13/717,993, filed on Dec. 18, 2012.

(60) Provisional application No. 61/581,146, filed on Dec. 29, 2011, provisional application No. 61/645,696, filed on May 11, 2012.

(51) Int. Cl.

| | | |
|---|---|---|
| *A61K 31/4184* | (2006.01) | |
| *A61K 38/06* | (2006.01) | |
| *A61K 47/32* | (2006.01) | |
| *A61K 9/10* | (2006.01) | |
| *A61K 38/05* | (2006.01) | |
| *A61K 38/07* | (2006.01) | |
| *A61K 45/06* | (2006.01) | |
| *A61K 9/14* | (2006.01) | |
| *A61K 9/16* | (2006.01) | |
| *A61K 31/403* | (2006.01) | |
| *A61K 31/4178* | (2006.01) | |
| *A61K 31/439* | (2006.01) | |
| *A61K 31/4709* | (2006.01) | |
| *A61K 31/497* | (2006.01) | |
| *A61K 31/501* | (2006.01) | |
| *A61K 31/519* | (2006.01) | |
| *A61K 31/549* | (2006.01) | |
| *A61K 31/55* | (2006.01) | |
| *A61K 31/7068* | (2006.01) | |
| *A61K 31/708* | (2006.01) | |

(52) U.S. Cl.
CPC .............. *A61K 9/10* (2013.01); *A61K 31/4184* (2013.01); *A61K 47/32* (2013.01); *A61K 38/06* (2013.01); *A61K 38/05* (2013.01); *A61K 38/07* (2013.01); *A61K 45/06* (2013.01); *A61K 9/146* (2013.01); *A61K 9/1635* (2013.01); *A61K 31/403* (2013.01); *A61K 31/4178* (2013.01); *A61K 31/439* (2013.01); *A61K 31/4709* (2013.01); *A61K 31/497* (2013.01); *A61K 31/501* (2013.01); *A61K 31/519* (2013.01); *A61K 31/549* (2013.01); *A61K 31/55* (2013.01); *A61K 31/7068* (2013.01); *A61K 31/708* (2013.01)

(58) Field of Classification Search
CPC ... A61K 31/4184; A61K 38/06; A61K 47/32; A61K 9/10

See application file for complete search history.

(56) References Cited

U.S. PATENT DOCUMENTS

| | | |
|---|---|---|
| 5,830,867 A | 11/1998 | Bhatnagar et al. |
| 5,935,982 A | 8/1999 | Dykstra et al. |
| 6,042,847 A | 3/2000 | Kerc et al. |
| 6,235,493 B1 | 5/2001 | Bissell et al. |
| 6,369,091 B1 | 4/2002 | Sircar et al. |
| 6,388,093 B1 | 5/2002 | Chamberlain et al. |
| 6,599,528 B1 | 7/2003 | Rosenberg et al. |
| 6,703,403 B2 | 3/2004 | Norbeck et al. |
| 6,846,802 B2 | 1/2005 | Chen et al. |
| 6,881,741 B2 | 4/2005 | Chan Chun Kong et al. |
| 6,919,366 B2 | 7/2005 | Sircar et al. |
| 6,923,988 B2 | 8/2005 | Patel et al. |
| 7,065,453 B1 | 6/2006 | Diller et al. |
| 7,141,574 B2 | 11/2006 | Beaulieu et al. |
| 7,183,270 B2 | 2/2007 | Cherney et al. |
| 7,488,832 B2 | 2/2009 | Cole et al. |
| 7,659,270 B2 | 2/2010 | Bachand et al. |
| 7,704,992 B2 | 4/2010 | Bachand et al. |
| 7,728,027 B2 | 6/2010 | Pack et al. |
| 7,732,457 B2 | 6/2010 | Malamas et al. |
| 7,741,347 B2 | 6/2010 | Bachand et al. |
| 7,745,636 B2 | 6/2010 | Bachand et al. |
| 7,759,495 B2 | 7/2010 | Bachand et al. |
| 7,763,731 B2 | 7/2010 | Rockway et al. |

(Continued)

FOREIGN PATENT DOCUMENTS

| | | |
|---|---|---|
| BR | PI0401908 A | 1/2006 |
| DE | 75755 C | 6/1894 |

(Continued)

OTHER PUBLICATIONS

Liu, R. Water-Insoluble Drug Formulation, Second Edition; CRC Press, 2008, pp. 499-503; 8 pages.*

(Continued)

*Primary Examiner* — Ernst V Arnold
(74) *Attorney, Agent, or Firm* — Xu Zhang

(57) ABSTRACT

The present invention features solid compositions comprising a selected HCV inhibitor in an amorphous form. In one embodiment, the selected HCV inhibitor is formulated in an amorphous solid dispersion which comprises a pharmaceutically acceptable hydrophilic polymer and preferably a pharmaceutically acceptable surfactant.

5 Claims, No Drawings

(56) References Cited

U.S. PATENT DOCUMENTS

| | | |
|---|---|---|
| 7,906,655 B2 | 3/2011 | Belema et al. |
| 8,025,899 B2 | 9/2011 | Berndl et al. |
| 8,088,368 B2 | 1/2012 | Guo et al. |
| 8,101,643 B2 | 1/2012 | Qiu et al. |
| 2002/0183319 A1 | 12/2002 | Liang et al. |
| 2003/0004203 A1 | 1/2003 | Sircar et al. |
| 2003/0100582 A1 | 5/2003 | Sircar et al. |
| 2003/0195228 A1 | 10/2003 | Chen et al. |
| 2004/0013697 A1 | 1/2004 | Berndl et al. |
| 2004/0229776 A1 | 11/2004 | Chen et al. |
| 2005/0075343 A1 | 4/2005 | Sircar et al. |
| 2005/0084529 A1 | 4/2005 | Rosenberg et al. |
| 2005/0197375 A1 | 9/2005 | Sircar et al. |
| 2006/0003942 A1 | 1/2006 | Tung et al. |
| 2006/0052602 A1 | 3/2006 | Kim et al. |
| 2006/0058317 A1 | 3/2006 | Gravestock et al. |
| 2006/0105997 A1 | 5/2006 | Arrington et al. |
| 2007/0004741 A1 | 1/2007 | Apodaca et al. |
| 2007/0142434 A1 | 6/2007 | Sandanayaka et al. |
| 2007/0197558 A1 | 8/2007 | Betebenner et al. |
| 2007/0218138 A1 | 9/2007 | Bittorf et al. |
| 2007/0232627 A1 | 10/2007 | Betebenner et al. |
| 2007/0232645 A1 | 10/2007 | Rockway et al. |
| 2007/0299068 A1 | 12/2007 | Karp et al. |
| 2008/0044379 A1 | 2/2008 | Bachand et al. |
| 2008/0044380 A1 | 2/2008 | Bachand et al. |
| 2008/0050336 A1 | 2/2008 | Bachand et al. |
| 2008/0075696 A1 | 3/2008 | Parsons et al. |
| 2008/0221107 A1 | 9/2008 | Giordanetto et al. |
| 2008/0299075 A1 | 12/2008 | Bachand et al. |
| 2008/0311075 A1 | 12/2008 | Bachand et al. |
| 2009/0004111 A1 | 1/2009 | Rice et al. |
| 2009/0041716 A1 | 2/2009 | Kim et al. |
| 2009/0043107 A1 | 2/2009 | Pack et al. |
| 2009/0068140 A1 | 3/2009 | Bachand et al. |
| 2009/0093456 A1 | 4/2009 | Arnold et al. |
| 2009/0104151 A1 | 4/2009 | Hanson et al. |
| 2009/0181902 A1 | 7/2009 | Desai et al. |
| 2009/0202478 A1 | 8/2009 | Bachand et al. |
| 2009/0202483 A1 | 8/2009 | Bachand et al. |
| 2009/0269305 A1 | 10/2009 | Seiwert et al. |
| 2010/0021540 A1 | 1/2010 | Gopinathan et al. |
| 2010/0029666 A1 | 2/2010 | Harper et al. |
| 2010/0055071 A1 | 3/2010 | Leivers et al. |
| 2010/0068176 A1 | 3/2010 | Belema et al. |
| 2010/0080772 A1 | 4/2010 | Belema et al. |
| 2010/0143499 A1 | 6/2010 | Condon |
| 2010/0144608 A1 | 6/2010 | Yigin et al. |
| 2010/0158862 A1 | 6/2010 | Kim et al. |
| 2010/0160355 A1 | 6/2010 | Degoey et al. |
| 2010/0168138 A1 | 7/2010 | Degoey et al. |
| 2010/0168384 A1 | 7/2010 | McDaniel et al. |
| 2010/0215616 A1 | 8/2010 | Romine et al. |
| 2010/0215618 A1 | 8/2010 | Carter et al. |
| 2010/0221214 A1 | 9/2010 | Or et al. |
| 2010/0221215 A1 | 9/2010 | Qiu et al. |
| 2010/0221216 A1 | 9/2010 | Or et al. |
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0249190 A1 | 9/2010 | Lopez et al. |
| 2010/0260708 A1 | 10/2010 | Belema et al. |
| 2010/0260715 A1 | 10/2010 | Or et al. |
| 2010/0266543 A1 | 10/2010 | Qiu et al. |
| 2010/0267634 A1 | 10/2010 | Donner et al. |
| 2010/0303755 A1 | 12/2010 | Lopez et al. |
| 2010/0310512 A1 | 12/2010 | Guo et al. |
| 2010/0316607 A1 | 12/2010 | Or et al. |
| 2010/0317568 A1 | 12/2010 | Degoey et al. |
| 2011/0008288 A1 | 1/2011 | Or et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |
| 2011/0077280 A1 | 3/2011 | Bender et al. |
| 2011/0092415 A1 | 4/2011 | Degoey et al. |
| 2011/0112100 A1 | 5/2011 | Milbank et al. |
| 2011/0136799 A1 | 6/2011 | Chern et al. |
| 2011/0142798 A1 | 6/2011 | Qiu et al. |
| 2011/0150827 A1 | 6/2011 | Dousson et al. |
| 2011/0152246 A1 | 6/2011 | Buckman et al. |
| 2011/0189129 A1 | 8/2011 | Qiu et al. |
| 2011/0195044 A1 | 8/2011 | Romine |
| 2011/0207660 A1 | 8/2011 | Sheth et al. |
| 2011/0207699 A1 | 8/2011 | Degoey et al. |
| 2011/0217261 A1 | 9/2011 | Or et al. |
| 2011/0218175 A1 | 9/2011 | Or et al. |
| 2011/0223134 A1 | 9/2011 | Nair et al. |
| 2011/0237579 A1 | 9/2011 | Li et al. |
| 2011/0237636 A1 | 9/2011 | Belema et al. |
| 2011/0250176 A1 | 10/2011 | Lemm et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0294819 A1 | 12/2011 | Lopez et al. |
| 2011/0300104 A1 | 12/2011 | Qiu et al. |
| 2011/0306541 A1 | 12/2011 | Delaney, IV et al. |
| 2011/0312973 A1 | 12/2011 | Liepold et al. |
| 2012/0004196 A1 | 1/2012 | Degoey et al. |
| 2012/0028978 A1 | 2/2012 | Zhong et al. |
| 2012/0039848 A1 | 2/2012 | Qiu et al. |
| 2012/0040977 A1 | 2/2012 | Li et al. |
| 2012/0076756 A1 | 3/2012 | Qiu et al. |
| 2012/0114600 A1 | 5/2012 | McKinnell et al. |
| 2012/0122864 A1 | 5/2012 | Zhong et al. |
| 2012/0172290 A1* | 7/2012 | Krueger et al. ............... 514/4.3 |
| 2012/0258909 A1 | 10/2012 | Liepold et al. |
| 2012/0264780 A1 | 10/2012 | Kullmann et al. |
| 2014/0212487 A1 | 7/2014 | Mogalian et al. |

FOREIGN PATENT DOCUMENTS

| | | |
|---|---|---|
| EP | 1880715 | 1/2008 |
| EP | 2242751 A1 | 10/2010 |
| JP | 2003282270 A | 10/2003 |
| JP | 2007320925 A | 12/2007 |
| JP | 2010126571 A | 6/2010 |
| RU | 2286343 C2 | 10/2006 |
| WO | WO-9427627 A1 | 12/1994 |
| WO | WO-9961020 A1 | 12/1999 |
| WO | WO-0000179 A1 | 1/2000 |
| WO | WO-0012521 A1 | 3/2000 |
| WO | WO-0214314 A2 | 2/2002 |
| WO | WO-03082186 A2 | 10/2003 |
| WO | WO-2004005283 A1 | 1/2004 |
| WO | WO-2004014313 A2 | 2/2004 |
| WO | WO-2004014852 A2 | 2/2004 |
| WO | WO-2004014852 A3 | 4/2004 |
| WO | WO-2004014313 A3 | 12/2005 |
| WO | WO-2005123076 A2 | 12/2005 |
| WO | WO-2006020951 A1 | 2/2006 |
| WO | WO-2006033703 A1 | 3/2006 |
| WO | WO-2006093867 A1 | 9/2006 |
| WO | WO-2006133326 A1 | 12/2006 |
| WO | WO-2007070556 A2 | 6/2007 |
| WO | WO-2007070600 A2 | 6/2007 |
| WO | WO-2007076034 A2 | 7/2007 |
| WO | WO-2007076035 A2 | 7/2007 |
| WO | WO-2007081517 A2 | 7/2007 |
| WO | WO-2007082554 A1 | 7/2007 |
| WO | WO-2007070556 A3 | 8/2007 |
| WO | WO-2007081517 A8 | 9/2007 |
| WO | WO-2007070600 A3 | 11/2007 |
| WO | WO-2007131366 A1 | 11/2007 |
| WO | WO-2007144174 A1 | 12/2007 |
| WO | WO-2008014236 A1 | 1/2008 |
| WO | WO-2008014238 A2 | 1/2008 |
| WO | WO-2008021927 A2 | 2/2008 |
| WO | WO-2008021928 A2 | 2/2008 |
| WO | WO-2008021936 A2 | 2/2008 |
| WO | WO-2008021928 A3 | 3/2008 |

(56) References Cited

FOREIGN PATENT DOCUMENTS

| | | |
|---|---|---|
| WO | WO-2008021936 A3 | 4/2008 |
| WO | WO-2008021927 A3 | 5/2008 |
| WO | WO-2008064218 A2 | 5/2008 |
| WO | WO-2008070447 A2 | 6/2008 |
| WO | WO-2008074450 A2 | 6/2008 |
| WO | WO-2008064218 A3 | 10/2008 |
| WO | WO-2008128121 A1 | 10/2008 |
| WO | WO-2008133753 A2 | 11/2008 |
| WO | WO-2008144380 A1 | 11/2008 |
| WO | WO-2009003009 A1 | 12/2008 |
| WO | WO-2009020534 A2 | 2/2009 |
| WO | WO-2009020825 A1 | 2/2009 |
| WO | WO-2009020828 A1 | 2/2009 |
| WO | WO-2008070447 A3 | 3/2009 |
| WO | WO-2009050289 A2 | 4/2009 |
| WO | WO-2009093082 A1 | 7/2009 |
| WO | WO-2009094224 A1 | 7/2009 |
| WO | WO-2009102318 A1 | 8/2009 |
| WO | WO-2009102325 A1 | 8/2009 |
| WO | WO-2009102568 A1 | 8/2009 |
| WO | WO-2009102633 A1 | 8/2009 |
| WO | WO-2009102694 A1 | 8/2009 |
| WO | WO-2009136290 A1 | 11/2009 |
| WO | WO-2009143361 A1 | 11/2009 |
| WO | WO-2009155709 A1 | 12/2009 |
| WO | WO-2010015090 A1 | 2/2010 |
| WO | WO-2010017035 A2 | 2/2010 |
| WO | WO-2010017401 A1 | 2/2010 |
| WO | WO 2010017432 * 2/2010 ............... A61K 9/20 | |
| WO | WO-2010030359 | 3/2010 |
| WO | WO-2010039793 A1 | 4/2010 |
| WO | WO-2010059858 A1 | 5/2010 |
| WO | WO-2010062821 A1 | 6/2010 |
| WO | WO-2010065668 A1 | 6/2010 |
| WO | WO-2010065674 A1 | 6/2010 |
| WO | WO-2010065681 A1 | 6/2010 |
| WO | WO-2010075376 A2 | 7/2010 |
| WO | WO-2010091413 A1 | 8/2010 |
| WO | WO-2010096302 A1 | 8/2010 |
| WO | WO-2010096462 A1 | 8/2010 |
| WO | WO-2010096777 A1 | 8/2010 |
| WO | WO 2010097229 * 9/2010 ............ C07D 417/04 | |
| WO | WO-2010099527 A1 | 9/2010 |
| WO | WO-2010111483 A1 | 9/2010 |
| WO | WO-2010111534 A1 | 9/2010 |
| WO | WO-2010111673 A1 | 9/2010 |
| WO | WO-2010115767 A1 | 10/2010 |
| WO | WO-2010117635 A1 | 10/2010 |
| WO | WO-2010117704 A1 | 10/2010 |
| WO | WO-2010117977 A1 | 10/2010 |
| WO | WO-2010120621 A1 | 10/2010 |
| WO | WO-2010120935 A1 | 10/2010 |
| WO | WO-2010122162 A1 | 10/2010 |
| WO | WO 2010017432 * 11/2010 ............ C07D 401/14 | |
| WO | WO-2010132538 A1 | 11/2010 |
| WO | WO-2010132601 A1 | 11/2010 |
| WO | WO-2010138368 A1 | 12/2010 |
| WO | WO-2010138488 A1 | 12/2010 |
| WO | WO-2010138790 A1 | 12/2010 |
| WO | WO-2010138791 A1 | 12/2010 |
| WO | WO-2010144646 A2 | 12/2010 |
| WO | WO-2010148006 A1 | 12/2010 |
| WO | WO-2011004276 A1 | 1/2011 |
| WO | WO-2011009084 A2 | 1/2011 |
| WO | WO-2011015658 A1 | 2/2011 |
| WO | WO-2011026920 A1 | 3/2011 |
| WO | WO-2011028596 A1 | 3/2011 |
| WO | WO-2011031904 A1 | 3/2011 |
| WO | WO-2011031934 A1 | 3/2011 |
| WO | WO-2011050146 A1 | 4/2011 |
| WO | WO-2011054834 A1 | 5/2011 |
| WO | WO-2011059850 A1 | 5/2011 |
| WO | WO-2011059887 A1 | 5/2011 |
| WO | WO-2011060000 A1 | 5/2011 |
| WO | WO-2011066241 A1 | 6/2011 |
| WO | WO-2011068941 A2 | 6/2011 |
| WO | WO-2011075439 A1 | 6/2011 |
| WO | WO-2011075607 A1 | 6/2011 |
| WO | WO-2011075615 A1 | 6/2011 |
| WO | WO-2011079327 A1 | 6/2011 |
| WO | WO-2011081918 A1 | 7/2011 |
| WO | WO-2011082077 A1 | 7/2011 |
| WO | WO-2011087740 A1 | 7/2011 |
| WO | WO-2011091417 A1 | 7/2011 |
| WO | WO-2011091446 A1 | 7/2011 |
| WO | WO-2011091532 A1 | 8/2011 |
| WO | WO-2011112429 A1 | 9/2011 |
| WO | WO-2011119853 A1 | 9/2011 |
| WO | WO-2011119858 A1 | 9/2011 |
| WO | WO-2011119860 A1 | 9/2011 |
| WO | WO-2011119870 A1 | 9/2011 |
| WO | WO-2011127350 A1 | 10/2011 |
| WO | WO-2011146401 A1 | 11/2011 |
| WO | WO-2011150243 A1 | 12/2011 |
| WO | WO-2011156543 A2 | 12/2011 |
| WO | WO-2011156578 A1 | 12/2011 |
| WO | WO-2012039717 A1 | 3/2012 |
| WO | WO-2012040389 A2 | 3/2012 |
| WO | WO-2012040923 A1 | 4/2012 |
| WO | WO-2012040924 A1 | 4/2012 |
| WO | WO-2012041014 A1 | 4/2012 |
| WO | WO-2012041227 A1 | 4/2012 |
| WO | WO-2012050848 A1 | 4/2012 |
| WO | WO-2012050850 A1 | 4/2012 |
| WO | WO-2012068234 A2 | 5/2012 |
| WO | WO-2012074437 A2 | 6/2012 |
| WO | WO-2012087976 A2 | 6/2012 |

OTHER PUBLICATIONS

Abagyan R., et al., "ICM—A New Method for Protein Modeling and Design: Applications to Docking and Structure Prediction from the Distorted Native Conformation," Journal of Computational Chemistry, 1994, vol. 15 (5), pp. 488-506.

Adjabeng G., et al., "Novel Class of Tertiary Phosphine Ligands Based on a Phospha-adamantane Framework and use in the Suzuki cross-Coupling Reactions of Aryl Halides Under Mild Conditions," Organic Letters, 2003, vol. 5 (6), pp. 953-955.

Adjabeng G., et al., "Palladium Complexes of 1,3,5,7-tetramethyl-2,4,8-trioxa-6-phenyl-6-phosphaadamantane: Synthesis, Crystal Structure and Use in the Suzuki and Sonogashira Reactions and the a-Arylation of Ketones," The Journal of Organic Chemistry, 2004, vol. 69 (15), pp. 5082-5086.

Aldous D.J., et al., "A Simple Enantioselective Preparation of (2S,5S)-2,5-diphenylpyrrolidine and Related Diaryl Amines," Tetrahedron Asymmetry, 2000, vol. 11, pp. 2455-2462.

Alesso E.N., et al., "Synthesis of Diastereoisomeric 1,2,3-Triphenylindans," Australian Journal of Chemistry, 1997, vol. 50, pp. 149-152.

Altschuel S.F., et al., "Basic Local Alignment Search Tool," Journal of Molecular Biology, 1990, 215, 403-410.

Altschul S.F., et al., "Gapped BLAST and PSI-BLAST: A New Generation of Protein Database Search Programs," Nucleic Acids Research, 1997, 25 (17), 3389-3402.

Angiolini M., et al., "Synthesis of Azabicycloalkane Amino Acid Scaffolds as Reverse-Turn Inducer Dipeptide Mimics," European Journal Organic Chemistry, 2000, pp. 2571-2581.

Baker D., et al., "Protein Structure Prediction and Structural Genomics," Science, 2001, vol. 294, pp. 93-96.

Bartenschlager R., "Hepatitis C Virus Molecular Clones: From cDNA to Infectious Virus Particles in Cell Culture," Current Opinion in Microbiology, 2006, vol. 9 (4), pp. 416-422.

Bartenschlager R., "Hepatitis C Virus Replicons: Potential Role for Drug Development," Nature Reviews Drug Discovery, 2002, vol. 1 (11), pp. 911-916.

Boehm T., et al., "Uber Die Bildung Von Gamma-Piperidonderivaten Aus Azetessigester, Aromatischen Aldehyden und Aminen, Eine Modifikation Der Hantzschschen Pyridinsynthese," Pharmaceutical,1943, vol. 281, pp. 62-77.

(56) References Cited

OTHER PUBLICATIONS

Bohm H.J., "The Computer Program LUDI: A New Method for the De Novo Design of Enzyme Inhibitors," Journal of Computer-Aided Molecular Design, 1992, vol. 6, pp. 61-78.
Breitenbach J., et al., "Confocal Raman-Spectroscopy: Analytical Approach to Solid Dispersions and Mapping of Drugs," Pharmaceutical Research 1999, vol. 16 (7), pp. 1109-1113.
Brettle R., et al., "A Highly Efficient Enzymic Route to Novel Chiral Liquid Crystals based on 3-Aryl-2-cycloalken-1-ones," Journal of the Chemical Society, Chemical Communications, 1994, pp. 2305-2306.
Brunger A.T., et al., "Recent Developments for the Efficient Crystallographic Refinement of Macromolecular Structures," Current Opinion in Structural Biology, 1998, vol. 8, pp. 606-611.
Bundgaard H., "Design of Prodrugs", Elsevier Science Publishers, 1985, pp. 7-9 & 1-6 & 21-24.
Bundgaard H., ed., in: Design of Prodrugs, Elsevier Science, 1985, Table of Contents.
Charifson P.S., et al., "Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Stucture-Activity Relationships," Journal of Medicinal Chemistry, 2008, vol. 51, pp. 5243-5263.
Chiou W.L., et al., "Pharmaceutical Applications of Solid Dispersion Systems," Journal of Pharmaceutical Sciences, 1971, vol. 60 (9), pp. 1281-1302.
Chong J.M., et al., "Asymmetric Synthesis of trans.2,5-Diphenylpyrrolidine: A C2-Symmetric Chirai Amine," Tetrahedron Asymmetry, 1995, vol. 6 (2), pp. 409-418.
Clark W.M., et al., "A Highly Enantioselective Conjugate Reduction of 3-Arylinden-1-ones Using Bakers' Yeast for the Preparation of (S)-3-Arylindan-1-ones," Organic Letters, 1999, vol. 1 (11), pp. 1839-1842.
Clarke P.A., et al., "Pot, Atom and Step Economic (PASE) Synthesis of Highly Functionalized Piperidines: A Five-Component Condensation," Tetrahedron Letters, 2007, vol. 48, pp. 5209-5212.
Clarke P.A., et al., "Pot, Atom and Step Economic (PASE) Synthesis of Highly Substituted Piperidines:A Five-Component Condensation," Synthesis, 2008, No. 28, pp. 3530-3532.
Collado I., et al, "Stereoselective Addition of Grignard-Derived Organocopper Reagents to N-Acyliminium Ions: Synthesis of Enantiopure 5- and 4,5-Substituted Prolinates," Journal of Organic Chemistry, 1995, vol. 60, pp. 5011-5015.
Conte I., et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19, pp. 1779-1783.
Co-pending U.S. Appl. No. 13/404,429, filed Feb. 24, 2012.
Cornell, W.D., et al., "A Second Generation Force Field for the Simulation of Proteins, Nucleic Acids, and Organic Molecules," Journal of the American Chemical Society, 1995, vol. 117, pp. 5179-5197.
De Francesco R., et al., "Challenges and Successes in Developing New Therapies for Hepatitis C," Nature, 2005, vol. 436, pp. 953-960.
Dell'Erba C., et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-endo-Trig Cyclization," European Journal of Organic Chemistry, 2000, pp. 903-912.
Effenberger F., et al., "Synthesis, Structure, and Spectral Behavior of Donor-Acceptor Substituted Biphenyls," The Journal of Organic Chemistry, 1983, vol. 48, pp. 4649-4658.
Eldridge M.D., et al., "Empirical Scoring Functions: I. The Development of a Fast Empirical Scoring Function to Estimate the Binding Affinity of Ligands in Receptor Complexes," Journal of Computer Aided Molecular Design, 1997, vol. 11, pp. 425-445.
Eswar N., et al., "Comparative Protein Structure Modeling Using Modeller," Current Protocols in Bioinformatics, 2006, Suppl. 15, 5.6.1-5.6.30.

European Search Report for Application No. EP12155991, mailed on Mar. 29, 2012, 2 pages.
Excipients & Activities for Pharma, ExAct, No. 20, May 2008.
Fan X., et al., "An Efficient and Practical Synthesis of the HIV Protease Inhibitor Atazanavir via a Highly Diastereoselective Reduction Approach," Organic Process Research and Development, 2008, vol. 12 (1), pp. 69-75.
Feig M., et al., "Performance Comparison of Generalized Born and Poisson Methods in the Calculation of Electrostatic Solvation Energies for Protein Structures," Journal of Computational Chemistry, 2004, vol. 25 (2), pp. 265-284.
Fiedler., "Encyclopedia of Excipients for Pharmaceuticals, Cosmetics and Related Areas," 5th Edition, Hoepfner E.M., et al., eds., Editio Cantor Verlag Aulendorf, 2002, Table of Contents.
Fiser A., et al., "Modeling of Loops in Protein Structures," Protein Science, 2000, vol. 9 (9), pp. 1753-1773.
Forster A., et al., "Selection of Excipients for Melt Extrusion with Two Poorly Water-Soluble Drugs by Solubility Parameter Calculation and Thermal Analysis," 2001, vol. 226, pp. 147-161.
Galun E., et al., "Hepatitis C Virus Viremia in SCID-BNX Mouse Chimera," Journal of Infectious Diseases, 1995, vol. 172 (1), pp. 25-30.
Gastreich M., et al., "Ultrafast De Novo Docking Combining Pharmacophores and Combinatorics," Journal of Computer-Aided Molecular Design, 2006, vol. 20, pp. 717-734.
Gillet V., et al., "SPROUT: A Program for Structure Generation," Journal of Computer-Aided Molecular Design, 1993, vol. 7, pp. 127-153.
Gohlke H., et al., "Approaches to the Description and Prediction of the Binding Affinity of Small-Molecule Ligands to Macromolecular Receptors," Angewandte Chemie International Edition, 2002, vol. 41 (15), pp. 2644-2676.
Goodford P.J., "A Computational Procedure for Determining Energetically Favorable Binding Sites on Biologically Important Macromolecules," Journal of Medicinal Chemistry, 1985, vol. 28, pp. 849-857.
Goodsell D.S., et al., "Automated Docking of Substrates to Proteins by Simulated Annealing," Proteins: Structure, Function, and Genetic, 1990, vol. 8, pp. 195-202.
Gordon T.D., et al, "Synthetic Approaches to the Azole Peptide Mimetics," Tetrahedron Letters, 1993, vol. 34 (12), pp. 1901-1904.
Greene T.W., et al., in: Protective Groups in Organic Synthesis, 3rd Edition, John Wiley and Sons, Inc., 1999, Preface, Table of Contents, Abbreviations.
Greene T.W., et al., "Protection for the Amino Group," Protective Groups in Organic Synthesis, 1999, Third Edition, pp. 494-653.
Halperin I., et al., "Principles of Docking: An Overview of Search Algorithms and a Guide to Scoring Functions," Proteins: Structure, Function, and Generic, 2002, vol. 47, pp. 409-443.
Hartwig J.F., et al., "III.3.2 Palladium-Catalyzed Amination of Aryl Halides and Related Reactions," Handbook of Organopalladium Chemistry for Organic Synthesis, 2002, pp. 1051-1096.
Hoover J.E., Remington's Pharmaceutical Sciences, 15th Edition, 1975, Mack Publishing Co., Table of Contents.
Hubbard S.R., et al., "Src Autoinhibition: Let us Count the Ways," Nature Structural Biology, 1999, vol. 6 (8), pp. 711-714.
International Preliminary Report on Patentability and Written Opinion for Application No. PCT/US2009/069188, mailed on Jun. 29, 2011, 10 pages.
International Preliminary Report on Patentability and Written Opinion for the Application No. PCT/US2010/031102, mailed on Oct. 18, 2011, 7 pages.
International Preliminary Report on Patentability for Application No. PCT/US2009/069177, mailed on Jun. 29, 2011, 1 page.
International Search Report and Written Opinion for Application No. PCT/US2009/038077, mailed on Jan. 21, 2011, 16 pages.
International Search Report and Written Opinion for Application No. PCT/US2009/069177, mailed on Aug. 10, 2010, 17 pages.
International Search Report for Application No. PCT/US2009/069188, mailed on Jun. 8, 2010, 4 pages.
International Search Report for Application No. PCT/US2011/039769, mailed on Oct. 6, 2011, 4 pages.

(56) References Cited

OTHER PUBLICATIONS

International Search Report for Application No. PCT/US2011/056045, mailed on Apr. 2, 2012, 4 pages.
International Search Report for Application No. PCT/US2011/065206, mailed on May 22, 2012, 3 pages.
International Search Report for Application No. PCT/US2011/065215, mailed on Jun. 12, 2012, 3 pages.
International Search Report for Application No. PCT/US2011/065224, mailed on Jun. 12, 2012, 3 pages.
International Search Report for Application No. PCT/US2011/065239, mailed on Jul. 30, 2012, 3 pages.
International Search Report for Application No. PCT/US2011/065242, mailed on May 22, 2012, 3 pages.
International Search Report for Application No. PCT/US2011/065247, mailed on Jun. 12, 2012, 3 pages.
International Search Report for Application No. PCT/US2011/065486, mailed on Mar. 26, 2012, 3 pages.
International Search Report for Application No. PCT/US2012/070349, mailed on May 14, 2013, 8 pages.
International Search Report for the Application No. PCT/US2010/031102, mailed on Sep. 1, 2010, 4 pages.
Jacques et al., "Enantiomers, Racemates, and Resolutions," J. Wiley & Sons, Chapter 3, pp. 197-213, 1981.
Jeffrey J.L., et al., "Concise Synthesis of Pauciflorol F Using a Larock Annulation," Organic Letters, 2009, vol. 11 (23), pp. 5450-5453.
Jing Q., et al., "Bulky Achiral Triarylphosphines Mimic BINAP in Ru(II)—Catalyzed Asymmetric Hydrogenation of Ketones," Advanced Synthesis & Catalysis, 2005, vol. 347, pp. 1193-1197.
Jones G., et al., "Development and Validation of a Genetic Algorithm for Flexible Docking," Journal of Molecular Biology, 1997, vol. 267 (3), pp. 727-748.
Jones G., et al., "Docking Small-Molecule Ligands into Active Sites," Current Opinion in Biotechnology, 1995, vol. 6 (6), pp. 652-656.
Jones G., et al., "Molecular Recognition of Receptor Sites using a Genetic Algorithm with a Description of Desolvation," Journal of Molecular Biology, 1995, vol. 245 (1), pp. 43-53.
Khan A.T., et al., "Effects of Substituents in the B-Position of 1,3-Dicarbonyl Compounds in Bromodimethylsulfonium Bromide-Catalyzed Multicomponent Reactions: A Facile Access to Functionalized Piperidines," Journal of Organic Chemistry, 2008, vol. 73, pp. 8398-8402.
Kolykhalov A.A., et al., "Transmission of Hepatitis C by Intrahepatic Inoculation with Transcribed RNA," Science, 1997, vol. 277 (5325), pp. 570-574.
Kuethe J.T., et al., "Asymmetric Synthesis of 1,2,3-Trisubstituted Cyclopentanes and Cyclohexanes as Key Components of Substance P Antagonists," The Journal of Organic Chemistry, 2002, vol. 67 (17), pp. 5993-6000.
Kuntz I.D., et al., "A Geometric Approach to Macromolecule-Ligand Interactions," Journal of Molecular Biology, 1982, vol. 161 (2), pp. 269-288.
Lattman, E., "Use of the Rotation and Translation Functions," Meth. In Enzymol., 1985, 115, 55-77.
Li, Chuan-Ying., et al., "Olefination of Ketenes for the Enantioselective Synthesis of Allenes via an Ylide Route," Tetrahedron, 2007, vol. 63, pp. 8046-8053.
Lieberman L., et al., eds., Pharmaceutical Dosage Forms, vol. 1, Marcel Dekker, Inc., 1980, Table of Contents.
Louie J., et al., "Palladium-Catalyzed Amination of Aryl Triflates and Importance of Triflate Addition Rate," Journal of Organic Chemistry, 1997, vol. 62 (5), pp. 1268-1273.
L-selectride, Retrieved from the Intenet:<URL: http://en.wikipedia.org/w/index.php"oldid=488453454>.
Lucas S., et al., "In Vivo Active Aldosterone Synthase Inhibitors with Improved Aelectivity: Lead Optimization Providing a Series of Pyridine Substituted 3,4-Dihydro-1H-Quinolin-2-one Derivatives," Journal of Medicinal Chemistry, 2008, vol. 51 (24), pp. 8077-8087.

Marti-Renom M.A., et al., "Comparative Protein Structure Modeling of Genes and Genomes," Annual Review of Biophysics and Biomolecular Structure, 2000, vol. 29, pp. 291-325.
Masters K., "Spray Drying Handbook" 4th Edition, John Wiley & Sons, 1985, Table of Contents.
Masui M., et al., "A Practical Method for Asymmetric Borane Reduction of Prochiral Ketones Using Chiral Amino Alcohols and Trimethyl Borate," Synlett, 1997, pp. 273-274.
Matzeit A., et al., "Radical Tandem Cyclizations by Anodic Decarboxylation of Carboxylic Acids," Synthesis, 1995, pp. 1432-1444.
Mercer D.F., et al., "Hepatitis C Virus Replication in Mice with Chimeric Human Livers," Nature Medicine, 2001, vol. 7 (8), pp. 927-933.
Miranker A., et al., "Functionality Maps of Binding Sites: A Multiple Copy Simultaneous Search Method," Proteins, 1991, vol. 11 (1), pp. 29-34.
Misra M., et al., "Organocatalyzed Highly Atom Economic One Pot Synthesis of Tetrahydropyridines as Antimalarials," Bioorganic & Medicinal Chemistry, 2009, vol. 17, pp. 625-633.
Moinet C., et al., "Novel Non-Peptide Ligands for the Somatostatin $sst_3$ Receptor," Bioorganic & Medicinal Chemistry Letters, 2001, vol. 11 (8), pp. 991-995.
Muci A.R., et al., "Practical Palladium Catalysts for C—N and C—O Bond Formation," Topics in Current Chemistry, 2002, vol. 219, pp. 131-209.
Muri E.M.F., et al., "Pseudo-Peptides Derived From Isomannide As Potential Inhibitors Of Serine Proteases," Amino Acids, 2005, vol. 28 (4), pp. 413-419.
Navaza J., "AMoRe: An Automated Package for Molecular Replacement," Acta Crystallographica, 1994, vol. A50 (2), pp. 157-163.
Naylor E.M., et al., "3-Pyridylethanolamines: Potent And Selective Human B3 Adrenergic Receptor Agonists," Bioorganic & Medicinal Chemistry Letters, 1998, vol. 8 (21), pp. 3087-3092.
Nevar N.M., et al., "One Step Preparation of 1,4-Diketones from Methyl Ketones and a-Bromomethyl Ketones in the Presence of ZnCl2•t-BuOH•Et2NR as a Condensation Agent," Synthesis, 2000, vol. 9, pp. 1259-1262.
Nishibata Y., et al., "Confirmation of Usefulness of a Structure Construction Program Based on Three-Dimensional Receptor Structure for Rational Lead Generation," Journal of Medicinal Chemistry, 1993, vol. 36 (20), pp. 2921-2928.
Pak V.D., et al., "Catalytic Condensation of Schiff's Base With P-Methoxybenzal Acetone," Catalytic Synthesis of Organic Nitrate Compounds, 1970, vol. 68 (Part 4), pp. 66-71.
Peng T., et al., "Construction of a Library of Rhodol Fluorophores for Developing New Fluorescent Probes," Organic Letters, 2010, vol. 12 (3), pp. 496-499.
Penning T.D., et al, "Discovery and SAR of 2-(1-Propylpiperidin-4-yl)-1H-Benzimidazole-4-Carboxamide: A Potent Inhibitor of Poly(ADP-ribose) Polymerase (PARP) for the Treatment of Cancer," Bioorganic & Medicinal Chemistry, 2008, vol. 16(14), pp. 6965-6975.
Polymer Handbook, Brandrup J., et al., Eds., Interscience Publishers, 1975, Table of Contents, III-139-III-192.
Rao S.N., et al., "Validation Studies of the Site-Directed Docking Program LibDock," Journal of Chemical Information and Modeling, 2007, vol. 47 (6), pp. 2159-2171.
Rarey M., et al., "A Fast Flexible Docking Method using an Incremental Construction Algorithm," Journal of Molecular Biology, 1996, vol. 261 (3), pp. 470-489.
Rosen M.H., et al., "Contraceptive Agents from Cycloaddition Reactions of Diarylcyclopropenones and Diarylthiirene 1, 1-Dioxides," Journal of Medicinal Chemistry, 1976, vol. 19 (3), pp. 414-419.
Rosenberg J., et al., "Novel Therapeutic Delivery System," Journal of Controlled Release, 2003, vol. 87, pp. 198-308.
Rossmann M.G., "The Molecular Replacement Method: A Collection of Papers on the Use of Non-Crystallographic Symmetry" Gordon and Breach Science Publishers, 1972, Table of Contents.
Sali A., et al., "Comparative Protein Modelling by Satisfaction of Spatial Restraints," Journal of Molecular Biology, 1993, vol. 234 (3), pp. 779-815.

(56) References Cited

OTHER PUBLICATIONS

Sato H., et al., "Prediction of Multiple Binding Modes of the CDK2 Inhibitors, Anilinopyrazoles, Using the Automated Docking Programs GOLD, FlexX, and LigandFit: An Evaluation of Performance," Journal of Chemical Information and Modeling, 2006, vol. 46 (6), pp. 2552-2562.

Sato M., et al., "Efficient Preparation of Optically Pure $C_2$-Symmetrical Cyclic Amines for Chiral Auxiliary," Synthesis, 2004, vol. 9, pp. 1434-1438.

Sawyer J.S., et al., "Synthetic and Structure/Activity Studies on Acid-Substituted 2-Arylphenols:Discovery of 2-[2-Propyl-3-[3-[2-ethyl-4-(4-fluorophenyl)-5-hydroxyphenoxy]-propoxy]phenoxy] benzoic Acid, a High-Affinity Leukotriene B4 Receptor Antagonist," Journal of Medicinal Chemistry, 1995, vol. 38 (22), pp. 4411-4432.

Serajuddin A.T., "Solid Dispersion of Poorly Water-Soluble Drugs: Early Promises, Subsequent Problems, and Recent Breakthroughs," Journal of Pharmaceutical Sciences, 1999, vol. 88 (10), pp. 1058-1066.

Smith A.B., et al., "Indole Diterpene Synthetic Studies: Development of a Second-Generation Synthetic Strategy for (+)-Nodulisporic Acids A and B," Journal of Organic Chemistry, 2007, vol. 72 (13), pp. 4611-4620.

Smith D.C., et al., "Reissert Compound Chemistry. XXVI. The Syntheses of Bis-Benzylisoquinolines," Journal of Heterocyclic Chemistry, 1976, vol. 13, pp. 573-576.

Sousa S.F., et al., "Protein-Ligand Docking: Current Status and Future Challenges," Proteins, 2006, vol. 65 (1), pp. 15-26.

Sperling L. H., "Introduction to Physical Polymer Science," 2nd Edition, John Wiley & Sons, Inc., 1992, Table of Contents.

Sugawara M., et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119 (49), pp. 11986-11987.

Takagi S., et al., "Antimicrobial Agents From *Bletilla striata*," Phyrochemistry, 1983, vol. 22 (4), pp. 1011-1015.

Tatsumi K., et al., "Enzyme-Mediated Coupling of 3,4-Dichloroaniline and Ferulic Acid: A Model for Pollutant Binding to Humic Materials," Environmental Science & Technology, 1994, vol. 28, pp. 210-215.

Tellinghuisen T.L., et al., "Structure of the Zinc-Binding Domain of an Essential Component of the Hepatitis C Virus Replicase," Nature, 2005, vol. 435 (7040), pp. 374-379.

Thayer A. M., "Finding Solutions, Custom manufacturers take on drug solubility issues to help pharmaceutical firms move products through development," Chemical & Engineering News, 2010, vol. 88 (22), pp. 13-18.

Vagin A., et al., "MOLREP: An Automated Program for Molecular Replacement," Journal of Applied Crystallography, 1997, vol. 30, pp. 1022-1025.

Vallee R.J., et al., "Photoannelation Reactions of 3-(Alk-1-ynyl)cyclohept-2-en-1-ones," Helvetica Chimica Acta, 2010, vol. 93 (1), pp. 17-24.

Verboom W., et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49 (2), pp. 269-276.

Voigt R., "Pharmaceutical Technology" for Students and Professionals, 7th revised Edition, 2000, pp. 80-85.

Warren G.L., et al., "A Critical Assessment of Docking Programs and Scoring Functions," Journal of Medicinal Chemistry, 2006, vol. 49 (20), pp. 5912-5931.

Web Page for Antares Health Products, www.tpgs.com. Downloaded Jan. 31, 2013.

Willis M.C., et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.

Wolfe J.P., et al., "Palladium-Catalyzed Amination of Aryl Triflates," Journal of Organic Chemistry, 1997, vol. 62 (5), pp. 1264-1267.

Wu G.Y., et al., "A Novel Immunocompetent Rat Model of HCV Infection and Hepatitis," Gastroenterology, 2005, vol. 128 (5), pp. 1416-1423.

Xiao D., et al., "A Practical Synthetic Pathway to Polysubstituted Tetrahydropyridines via Multicomponent Reactions Catalyzed by $BF_3 \cdot OEt_2$," Synlett, 2005, vol. 10, pp. 1531-1534.

Xie Z.C., et al., "Transmission of Hepatitis C Virus Infection to Tree Shrews," Virology, 1998, vol. 244 (2), pp. 513-520.

Yanagi M., et al., "Transcripts from a Single Full-Length cDNA Clone of Hepatitis C Virus are Infectious when Directly Transfected into the Liver of a Chimpanzee," Proceedings of the National Academy of Sciences, 1997, vol. 94 (16), pp. 8738-8743.

Yu H., et al., "The Discovery of Novel Vascular Endothelial Growth Factor Receptor Tyrosine Kinases Inhibitors: Pharmacophore Modeling, Virtual Screening and Docking Studies," Chemical Biology and Drug Design, 2007, vol. 69 (3), pp. 204-211.

Zhang J., et al., "Stereoselective Bromination-Suzuki Cross-Coupling of Dehydroamino Acids To Form Novel Reverse-Turn Peptidomimetics: Substituted Unsaturated and Saturated Indolizidinone Amino Acids," Journal of the American Chemical Society, 2002, vol. 4 (23), pp. 4029-4032.

Zhu Q., et al., "Novel Robust Hepatitis C Virus Mouse Efficacy Model," Antimicrobial Agents and Chemotherapy, 2006, vol. 50 (10), pp. 3260-3268.

International Search Report for Application No. PCT/US2012/026456, mailed on Jun. 22, 2012, 3 pages.

Written Opinion for Application No. PCT/US2011/027511, mailed on Nov. 10, 2011, 6 pages.

Baird J.A., et al., "A Classification System to Assess the Crystallization Tendency of Organic Molecules from Undercooled Melts," Journal of Pharmaceutical Sciences, 2010, vol. 99 (9), pp. 3787-3806.

Gao M., et al., "Chemical Genetics Strategy Identifies an HCV NS5A Inhibitor with a Potent Clinical Effect," Nature, 2010, vol. 465 (7294), pp. 96-100.

Shamblin S.L., et al., "Characterization of the Time Scales of Molecular Motion in Pharmaceutically Important Glasses," Journal of Physical Chemistry B, 1999, vol. 103, pp. 4113-4121.

Van Eerdenbrugh B., et al., "Crystallization Tendency of Active Pharmaceutical Ingredients following Rapid Solvent Evaporation-Classification and Comparison with Crystallization Tendency from Undercooled Melts," Journal of Pharmaceutical Sciences, 2010, vol. 99 (9), pp. 3826-3838.

Buhler (Polyvinylpyrrolidone Excipients for Pharmaceuticals 2005, Spring pp. 66, 67, 85 and 100 in part). 6 pages.

Spray drying for Amorphous Dispersions ([online]); retrieved from: http://www.formexlic.com/pages/spray-drying-amorphous-dispersions on Feb. 13, 2014; 2 pages).

\* cited by examiner

SOLID COMPOSITIONS

This application is a continuation-in-part of U.S. patent application Ser. No. 13/717,993, filed Dec. 18, 2012, which claims priority from U.S. Provisional Patent Application Ser. No. 61/581,146, filed Dec. 29, 2011, and U.S. Provisional Patent Application Ser. No. 61/645,696, filed May 11, 2012. This application incorporates by reference the entire content of U.S. Patent Application Publication No. 2013/0172239.

FIELD OF THE INVENTION

The present invention relates to solid compositions comprising anti-HCV compounds and methods of using the same to treat HCV infection.

BACKGROUND

The hepatitis C virus (HCV) is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often inadequate. Therefore, there is a need for new drugs to treat HCV infection.

SUMMARY OF THE INVENTION

The present invention features solid compositions comprising (1) an HCV inhibitor selected from telaprevir (VX-950), BI-201335, TMC-435 (TMC-435350), vaniprevir (MK-7009), MK-5172, asunaprevir (BMS-650032), daclatasvir (BMS-790052), danoprevir, setrobuvir (ANA-598), tegobuvir (GS-333126 or GS-9190), GS-9451, mericitabine (R-4048), IDX-184, filibuvir (PF-00868554), PSI-7977, PSI-352938, BIT-225, boceprevir, GS-5885 or GS-9256 (hereinafter a "selected HCV inhibitor"); (2) a pharmaceutically acceptable hydrophilic polymer; and optionally (3) a pharmaceutically acceptable surfactant.

In one aspect, the present invention features a solid composition comprising a solid dispersion, wherein the solid dispersion comprises (1) a selected HCV inhibitor in an amorphous form, (2) a pharmaceutically acceptable hydrophilic polymer, and (3) a pharmaceutically acceptable surfactant, wherein the selected HCV inhibitor is telaprevir (VX-950), BI-201335, TMC-435 (TMC-435350), vaniprevir (MK-7009), MK-5172, asunaprevir (BMS-650032), daclatasvir (BMS-790052), danoprevir, setrobuvir (ANA-598), tegobuvir (GS-333126 or GS-9190), GS-9451, mericitabine (RG-7128 or R-4048), IDX-184, filibuvir (PF-00868554), PSI-7977, PSI-352938, BIT-225, boceprevir, GS-5885 or GS-9256. The surfactant can be, without limitation, either formulated in the solid dispersion or separately combined or mixed with the solid dispersion. Preferably, the hydrophilic polymer has a $T_g$ of at least 50° C. More preferably, the hydrophilic polymer has a $T_g$ of at least 80° C. Highly preferably, the hydrophilic polymer has a $T_g$ of at least 100° C. Hydrophilic polymers with $T_g$s of below 50° C., such as a polymer having a $T_g$ of at least 25° C., and/or surfactants having HLB values of below 10, can also be used.

In one embodiment of this aspect of the invention, the hydrophilic polymer is selected from homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, or polysaccharide. Non-limiting examples of suitable hydrophilic polymers include homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, graft copolymer of polyethylene glycol/polyvinyl caprolactam/polyvinyl acetate (e.g., Soluplus), polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, or xanthan gum, or a combination thereof. In some cases, sugar alcohols can be used in addition to, or in lieu of, hydrophilic polymers.

In another embodiment of this aspect of the invention, the surfactant is selected from polyoxyethylene castor oil derivates, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, or sorbitan fatty acid mono ester. Non-limiting examples of suitable surfactants include polyoxyethyleneglycol triricinoleate or polyoxyl 35 castor oil (Cremophor EL; BASF Corp.) or polyoxyethyleneglycol oxystearate such as polyethylenglycol 40 hydrogenated castor oil (Cremophor RH 40, also known as polyoxyl 40 hydrogenated castor oil or macrogolglycerol hydroxystearate) or polyethylenglycol 60 hydrogenated castor oil (Cremophor RH 60), mono fatty acid ester of polyoxyethylene sorbitan, such as mono fatty acid ester of polyoxyethylene (20) sorbitan, e.g. polyoxyethylene (20) sorbitan monooleate (Tween 80), polyoxyethylene (20) sorbitan monostearate (Tween 60), polyoxyethylene (20) sorbitan monopalmitate (Tween 40) or polyoxyethylene (20) sorbitan monolaurate (Tween 20), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate (e.g., lauroglycol FCC), D-alpha-tocopheryl polyethylene glycol 1000 succinate, sucrose monostearate, sucrose distearate, sucrose monolaurate, sucrose dilaurate, sorbitan mono laurate, sorbitan monooleate, sorbitan monopalnitate, or sorbitan stearate, or a combination thereof. Other suitable ionic or non-ionic surfactants may also be used.

In yet another embodiment of this aspect of the invention, the solid dispersion is an amorphous solid dispersion. In still another embodiment, the solid dispersion is an amorphous solid dispersion which comprises (1) the selected HCV inhibitor, (2) the hydrophilic polymer, and (3) the surfactant. In a further embodiment, the solid dispersion is a solid solution comprising (1) the selected HCV inhibitor, and (2) the hydrophilic polymer. In yet another embodiment, the solid dispersion is a solid solution comprising (1) the selected HCV inhibitor, (2) the hydrophilic polymer, and (3) the surfactant.

In yet another embodiment of this aspect of the invention, the hydrophilic polymer is a homopolymer or copolymer of N-vinyl pyrrolidone. Preferably, the hydrophilic polymer is copovidone.

In still another embodiment, the surfactant is D-alpha-tocopheryl polyethylene glycol 1000 succinate (vitamin E TPGS). In a further embodiment, the surfactant is lauroglycol FCC. In yet another embodiment, the surfactant is a combination of vitamin E TPGS and lauroglycol FCC. In still another embodiment, the surfactant is a sorbitan fatty acid ester, such as sorbitan mono laurate (Span 20). In another embodiment, the surfactant is selected from Tween 20, Tween 80, vitamin E TPGS, lauroglycol FCC, or a combination thereof.

In yet another embodiment, a solid composition of the invention comprises an amorphous solid dispersion or a solid solution which comprises (1) the selected HCV inhibitor, (2) copovidone, and (3) a surfactant selected from vitamin E TPGS, Span 20, or a combination thereof.

In another embodiment, a solid composition of the invention comprises an amorphous solid dispersion or a solid solution which comprises (1) the selected HCV inhibitor, (2) copovidone, and (3) a combination of vitamin E TPGS and lauroglycol FCC.

In still another embodiment, a solid composition of the invention comprises an amorphous solid dispersion or a solid solution which comprises (1) the selected HCV inhibitor, (2) copovidone, and (3) a surfactant selected from Tween 20 or Tween 80.

In another aspect, the present invention features processes of making a solid composition of the present invention. In one embodiment, the process comprises drying a volatile solvent in a liquid solution, wherein said solution comprises: (1) the selected HCV inhibitor; (2) a pharmaceutically acceptable hydrophilic polymer; and optionally (3) a pharmaceutically acceptable surfactant. The drying process can be carried out using any suitable solvent evaporation techniques including but not limited to spray-drying techniques.

In another embodiment, the process comprises solidifying a melt which comprises: (1) the selected HCV inhibitor; (2) a pharmaceutically acceptable hydrophilic polymer; and optionally (3) a pharmaceutically acceptable surfactant.

A solid composition of the invention may also contain other additives or ingredients, such as coloring agents, flavoring agents, lubricants or preservatives. A solid composition of the invention can be prepared into any suitable dosage forms, such as capsule, dragee, granule, powder, or tablet.

A solid composition of the invention may further comprise another anti-HCV agent, for example, an agent selected from HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors.

The present invention further features methods of using a solid composition of the present invention to treat HCV infection. The methods comprise administering a solid composition of the present invention to a patient in need thereof, thereby reducing the blood or tissue level of HCV virus in the patient.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The present invention features solid compositions comprising (1) a selected HCV inhibitor, (2) a pharmaceutically acceptable hydrophilic polymer, and optionally (3) a pharmaceutically acceptable surfactant, wherein the selected inhibitor is telaprevir (VX-950), BI-201335, TMC-435 (TMC-435350), vaniprevir (MK-7009), MK-5172, asunaprevir (BMS-650032), daclatasvir (BMS-790052), danoprevir, setrobuvir (ANA-598), tegobuvir (GS-333126 or GS-9190), GS-9451, mericitabine (R-4048), IDX-184, filibuvir (PF-00868554), PSI-7977, PSI-352938, BIT-225, boceprevir, GS-5885 or GS-9256. Formulating the selected HCV inhibitor in an amorphous form can increase the inherent drug solubility and dissolution rate, thereby enhancing the bioavailability of the compound.

Telaprevir (VX-950), BI-201335, TMC-435 (TMC-435350), vaniprevir (MK-7009), MK-5172, asunaprevir (BMS-650032), danoprevir, GS-9451, boceprevir and GS-9256 are HCV protease inhibitors; daclatasvir (BMS-790052) and GS-5885 are HCV NS5A inhibitors; and setrobuvir (ANA-598), tegobuvir (GS-333126 or GS-9190), mericitabine (R-4048), IDX-184, filibuvir (PF-00868554), PSI-7977, PSI-352938 (PSI-938), and BIT-225 are polymerase inhibitors. The chemical structures of these selected HCV inhibitors are provided below:

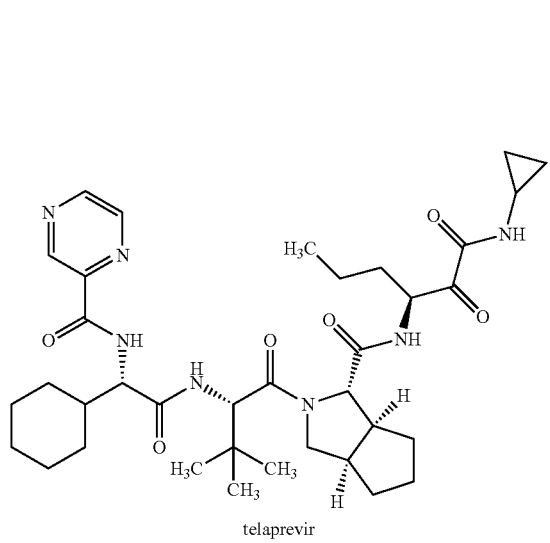
telaprevir
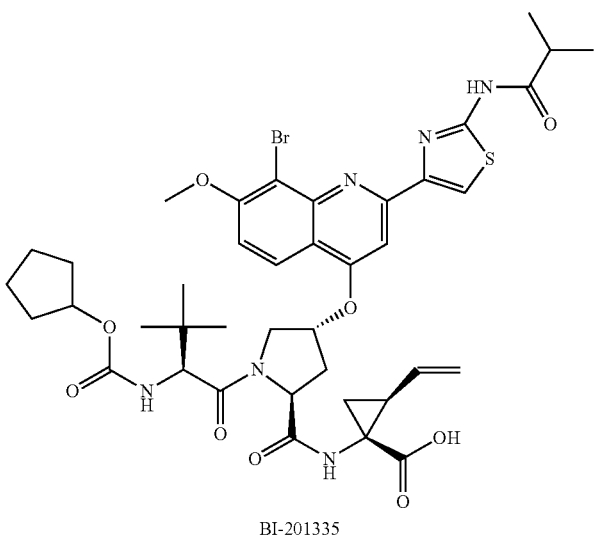
BI-201335
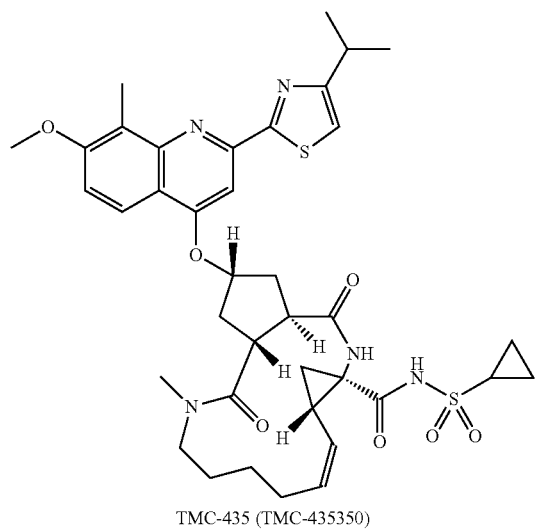
TMC-435 (TMC-435350)
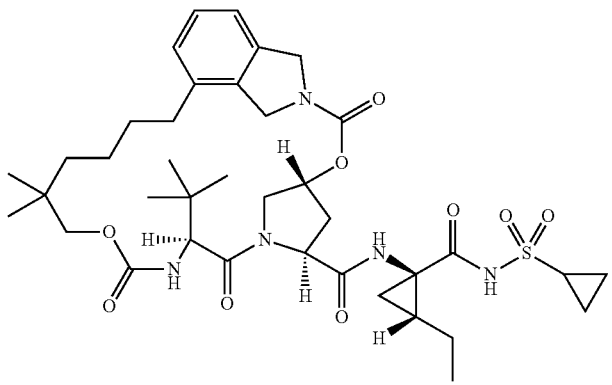
vaniprevir (MK-7009)
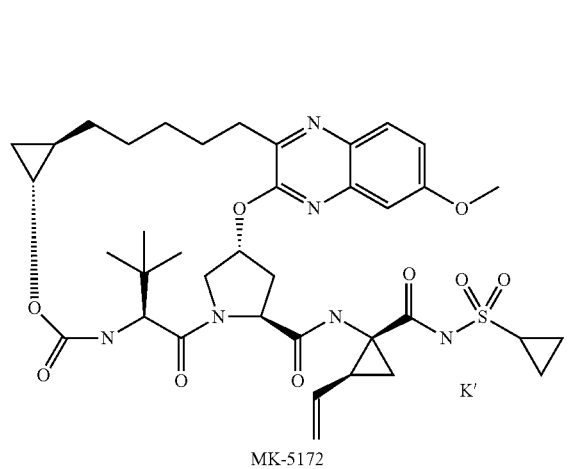
MK-5172
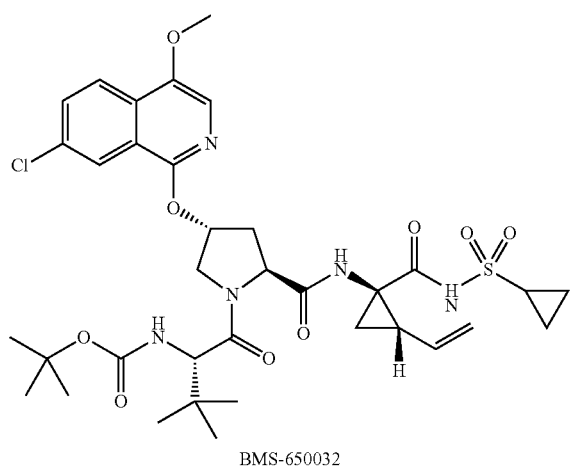
BMS-650032

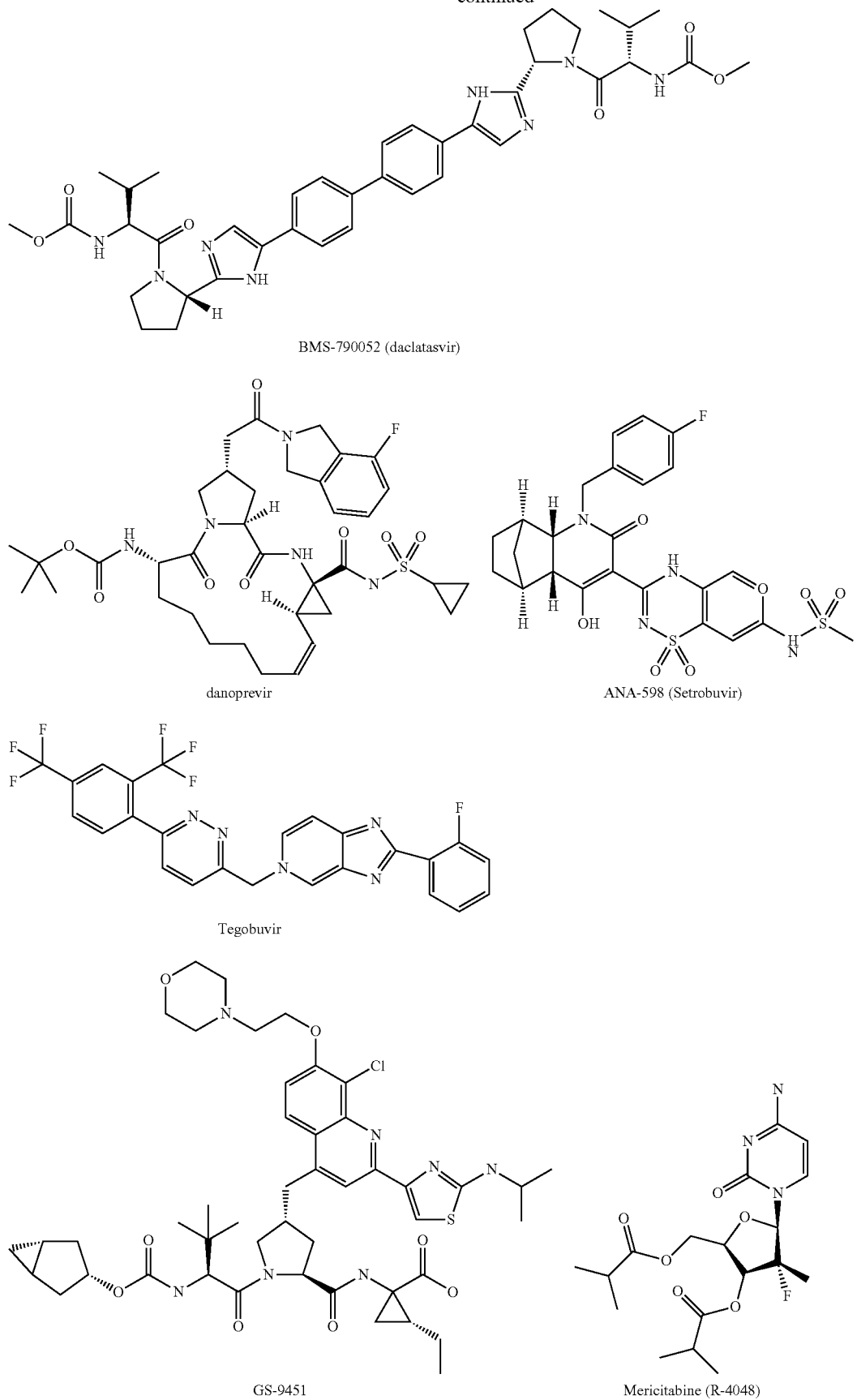

-continued
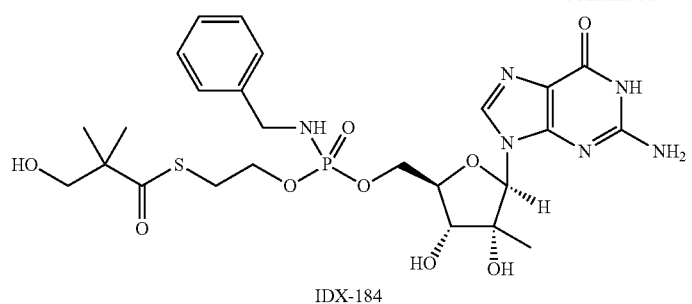
IDX-184
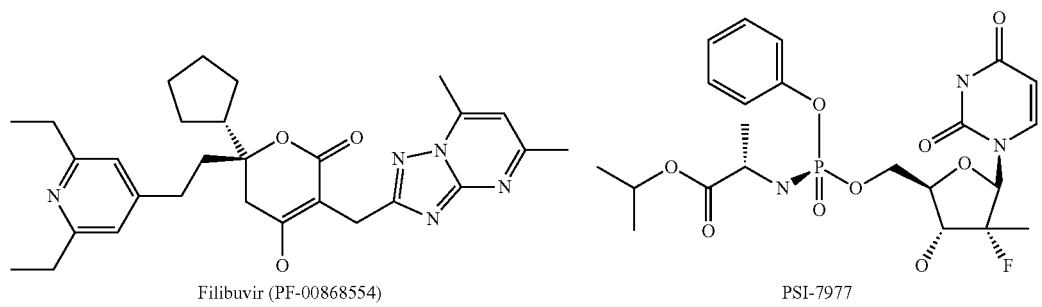
Filibuvir (PF-00868554)     PSI-7977
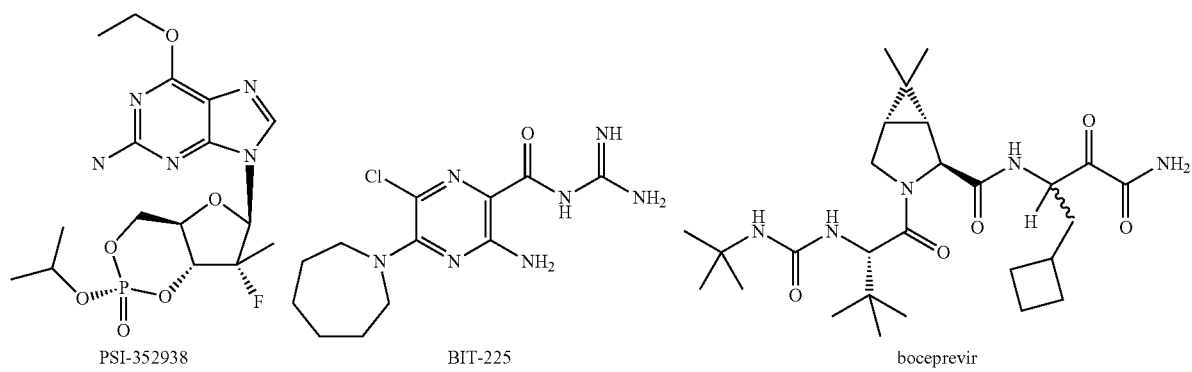
PSI-352938     BIT-225     boceprevir
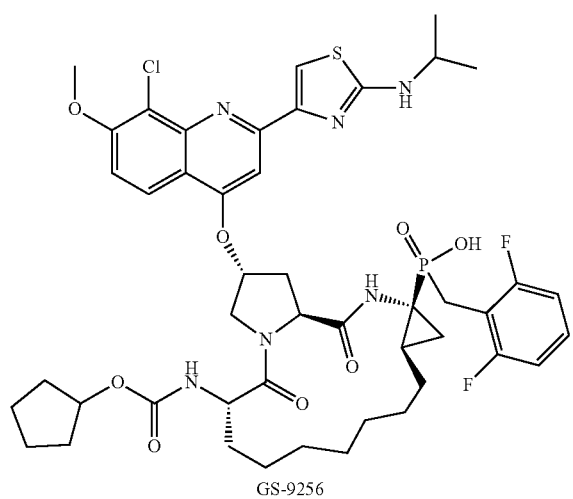
GS-9256

-continued

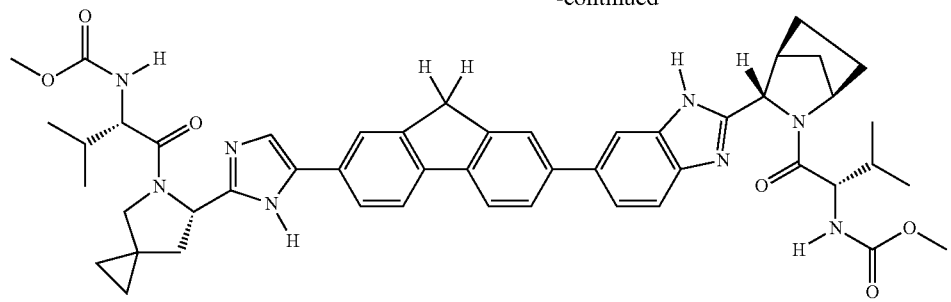

GS-5885

A non-limiting way to form an amorphous form of a selected HCV inhibitor described hereinabove is through the formation of solid dispersions with a polymeric carrier. The presence of hydrophilic polymer(s) and optional surfactant(s), as well as the dispersion of the selected HCV inhibitor in an amorphous form in a matrix containing the polymer(s), can significantly enhance the dissolution rate of the selected compound. In some cases, a solid dispersion formulation can also effectively maintain the selected HCV inhibitor in its supersaturation state to allow for better absorption.

As used herein, the term "solid dispersion" defines a system in a solid state (as opposed to a liquid or gaseous state) comprising at least two components, wherein one component is dispersed throughout the other component or components. For example, a selected HCV inhibitor described hereinabove can be dispersed in a matrix comprised of a pharmaceutically acceptable hydrophilic polymer(s) and a pharmaceutically acceptable surfactant(s). The term "solid dispersion" encompasses systems having small particles of one phase dispersed in another phase. These particles are often of less than 400 μm in size, such as less than 100, 10, or 1 μm in size. When a solid dispersion of the components is such that the system is chemically and physically uniform or homogenous throughout or consists of one phase (as defined in thermodynamics), such a solid dispersion is called a "solid solution." A glassy solution is a solid solution in which a solute is dissolved in a glassy solvent.

The terms "weight percent" or "percent by weight" or "% by weight" or "wt %" denote the weight of an individual component in a composition or mixture as a percentage of the weight of the composition or mixture.

Modern new chemical entities tend to have higher molecular weight, greater lipophilicity and lower aqueous solubility, all of which negatively affect oral bioavailability. Despite formulation advances leading to the commercialization of enabling technologies such as lipid-based drug delivery systems (e.g. SEDDS) and nano-particles, the delivery of poorly water-soluble compounds remains challenging because of the limitations associated with each approach. Utilizing an amorphous solid dispersion (ASD) is attractive not only because it can increase the pharmacokinetic exposure of otherwise poorly absorbed drugs, but also because the final product may be delivered to the patient as a tablet or capsule, which may provide greater chemical stability and improved patient convenience compared to liquid dosage forms.

For all formulation approaches it is imperative to understand the intrinsic physicochemical and biopharmaceutical properties of the active drug substance prior to or at the onset of development. To that end, the biopharmaceutical classification system (BCS) has been routinely utilized to assess oral absorption and guide formulation development. For ASD formulations, the solubility/permeability of the active pharmaceutical ingredient (API) as well as the long term physical stability of the amorphous drug products are often considered. Conceptually, there are three major factors that influence the physical stability of an ASD: thermodynamic driving force (difference in drug loading and the solubility of drug in matrix), molecular mobility, and activation barrier for crystallization. The present invention relies on the use of an innovative assessment tool to rank the intrinsic physical stability of amorphous drug substances, e.g., crystallization tendency of amorphous API.

The molecular mobility of an amorphous material, which is often characterized by the relaxation time constant or its reciprocal, molecular mobility, is considered by many as a principal factor in determining its physical stability. Kinetic characterization of amorphous materials has been a subject of growing research in pharmaceutical field. The fact that crystallization of amorphous phases proceeds much faster in the supercooled liquid states compared to the glassy states demonstrates the importance of molecular mobility. However significant differences in crystallization tendency have been observed across compounds that cannot be explained by mobility alone. For example, some amorphous phases crystallize almost immediately at the glass temperature, $T_g$ (e.g., progesterone, parabens, acetaminophen), some crystallize below $T_g$ in a relatively short time (e.g., griseofulvin, nifedipine), while others are quite stable. For some of the more stable amorphous phases, crystallization in the glassy state is often not observed and it does not proceed at a significant rate above $T_g$ without seeding. Theoretically, $T_g$ corresponds to the temperature of which the molecular relaxation time constant of the amorphous phase is equivalent to the experimental time scale. In light of these differences it has been postulated that, in addition to mobility, the thermodynamic driving force and activation barrier to crystallization contribute to the observed physical stability differences among these compounds.

Shamblin et al., J. Phys. Chem. B 103: 4113-4121 (1999), assessed molecular mobility of amorphous materials based on heat capacity measurements and the Adam-Gibbs model. This method allows calculation of molecular mobility using temperature-modulated differential scanning calorimetry (TMDSC) that is widely available in pharmaceutical laboratories together with the Adam-Gibbs model which has been used to characterize other materials, such as polymers and ceramics.

Using this method, the physical stability of pharmaceutically relevant compounds can be explored in an attempt to identify thermodynamic quantities critical to crystallization. Through this analysis, the calorimetric configurational entropy has been shown to be an important factor in determining crystallization tendency above the $T_g$.

The configurational entropy typically is a measure of the difference in the number of configurations between the amorphous and the crystalline phases. For molecules in the amorphous state to crystallize, they have to pack into a specific crystal lattice with defined configuration or orientation. Therefore, higher configurational entropy values suggest a lower probability that molecules are in the desirable orientation for packing into the crystal lattice. Hence, a meta-stable amorphous compound with larger configurational entropy tends to show greater physical stability. This is consistent with the observation that large molecules with numerous rotatable bonds are often more difficult to crystallize.

It has been hypothesized that the configurational entropy serves as a thermodynamic measurement of the probability of nucleation while the molecular mobility dictates the rate at which a molecule can change its configurations and serves as a kinetic measurement of nucleation. Similar arguments may be applied to the rate of crystal growth as well. Therefore, these two quantities can be used to assess the intrinsic physical stability risk for the amorphous APIs.

Based on experimental crystallization observations of different compounds, Baird et al., J. PHARM. SCI. 99: 3787-3806 (2010); and Eerdenbrugh et al., J. PHARM. SCI. 99: 3826-3838 (2010) proposed a classification system for assessing the crystallization tendency of amorphous systems. However, crystallization experiments take relatively long time and the results are influenced by both intrinsic and extrinsic factors. The present invention utilizes the two above intrinsic properties and a different amorphous classification system (ACS) to assess the physical stability of amorphous drug candidates. The two intrinsic molecular properties can be calculated from a single convenient calorimetry measurement.

The structural flexibility and mobility of a molecule can be used to predict whether a compound will be kinetically stable as an amorphous phase. A physically stable amorphous API may play a role in the physical stability of a formulated ASD.

In the ACS used in the present invention, molecules can be categorized into four categories, as follows:

Class I: Stable amorphous solid/poor crystallizer, and High configurational entropy and low molecular mobility (excellent candidates for developing ASD formulations)

Class II: Intermediate amorphous stability/crystallizer, and High configurational entropy but high molecular mobility Class III: Intermediate amorphous stability/crystallizer, and Low molecular mobility but low configurational entropy Class IV: Unstable amorphous solid/good crystallizer, and Low configurational entropy and high molecular mobility (poor candidates for developing ASD formulations)

Mobility is highly dependent on the temperature but identical at the $T_g$ for all glasses. Molecular mobility is usually represented by the VTF equation in the supercooled liquid state and by the AGV equation in the glassy state as follows:

$$\tau(T) = \tau_0 \exp\left(\frac{DT_0}{T - T_0}\right) \quad \text{(VTF equation)}$$

$$\tau(T, T_f) = \tau_0 \exp\left(\frac{DT_0}{T - (T/T_f)T_0}\right) \quad \text{(AGV equation)}$$

where $\tau$ is the relaxation time constant, $\tau_0$ is a constant assumed to equal to $10^{-14}$ second, D is the strength parameter, and $T_0$ is the temperature with zero molecular mobility ($\tau = \infty$), which is called the Kauzmann temperature and is the temperature where the equilibrium supercooled liquid (i.e. ideal glass) has the same entropy as the crystalline state. $T_f$ is the fictive temperature, which is the temperature where the ideal glass has the same configurational entropy as a real glass at a given temperature (T). It is worth noting that, by definition, at $T_g$ the relaxation time constants are the same for all amorphous systems (i.e. $\tau_g = 100$ sec). The strength parameter D can be used as a convenient representation of molecular mobility at $T < T_g$.

At the glass transition temperature, $T_g$, the following relationship holds, which can be obtained via the VTF equation:

$$\frac{T_g}{T_0} = \frac{D}{\ln(\tau_g/\tau_0)} + 1$$

where $\tau_g$ is the relaxation time constant at $T_g$. D and $T_o$ are not independent and that $T_g/T_0$ is a parameter associated with the strength parameter D. In many theoretical treatments, $\tau_0$ is assumed to be $10^{-14}$ sec, therefore $\ln(\tau_g/\tau_0) = \ln(10^{16}) = 36.84$ is a constant.

Given that $T_g$ is the temperature associated with a constant mobility (i.e. $\tau = 100$ sec) while $T_0$ is a temperature associated with zero mobility for ideal glasses, the ratio of $T_g/T_0$, and therefore the value D, represent how fast the molecular mobility of an ideal glass decreases with lowering temperature. The higher the D value, the slower the rate of decrease of molecular mobility with lowering temperature, thus favors crystallization.

It can be further shown for ideal glasses, that:

$$\ln[\tau_T/\tau_0] = \frac{DC(T_g/T)}{D + C(1 - T_g/T)}$$

Where $C = \ln(\tau_g/\tau_0) = 36.84$. Given $C > 0$, $T_g/T > 1$, hence at a common temperature represented on the scale of $T_g/T$, the molecular mobility of the ideal glass is expected to be higher for a glass with larger D value. Opposite trend is true in the supercooled liquid state above $T_g$. Therefore the strength parameter serves a convenient indicator for molecular mobility in ideal glasses: the larger the D value, the higher the mobility (at identical $T_g/T$).

"Ideal freshly prepared glass" is one that is melt-quenched with sufficiently high cooling rates, such that no structural relaxation has occurred at temperatures below the glass transition temperature. In such "ideal freshly prepared glasses", the fictive temperature $T_f$ equals its glass transition temperature, $T_g$. Therefore molecular relaxation time constant for an "ideal freshly prepared glass" may be derived based on the AGV equation:

$$\tau(T < T_g) = \tau_0 \exp\left(\frac{T_g}{T} \cdot \frac{DT_0}{T_g - T_0}\right) = \tau_0 \exp\left(\frac{T_g}{T} \cdot \ln(\tau_g/\tau_0)\right)$$

The above equation demonstrates the Arrhenius behavior with regard to the temperature dependence of molecular relaxation time constants in these systems. It is further noted that, at the same value of $T_g/T$, the molecular relaxation time constant or mobility is the same for all "ideal freshly prepared glasses", regardless of other characteristics of the system. At the first glance, the strength parameter does not appear to be relevant to the magnitude of molecular mobility.

However, configurations in real glasses are not fully arrested. Molecular motions do occur on a longer time scale which leads to structural relaxation or aging. As a result, molecular mobility of real glasses becomes a function of aging time. In reality, when a liquid is quench-cooled, structural relaxation has already occurred in any freshly prepared glass. During the process of aging, the strength parameter D plays a role in the evolution of molecular mobility, from the "ideal freshly prepared glass" where D is of no relevance, to the ideal glass where a higher D value is associated with a higher mobility. The evolution of the molecular mobility reveals a similar relationship between mobility and strength parameter, i.e. higher molecular mobility is dictated by a higher D value during this evolution process.

The configurational entropy at $T_g$ would serve as a good indicator for this parameter for two reasons: (1) Amorphous pharmaceuticals are often practically stored below the glass transition temperature; (2) Configurational entropy for "ideal freshly prepared glass" is temperature independent at $T<T_g$.

During storage, the configurational entropy continuously decreases as structural relaxation occurs. However the decrease in entropy slows down with time and is far from the values in the ideal glass, even when considering the physical aging over the entire two year's of shelf-life.

To determine configurational entropy, instrument such as TMDSC can be calibrated to obtain accurate measurements of heat capacity. In addition, a conventional DSC scan may provide significant insight on this thermodynamic quantity. It has been observed that the change in configurational heat capacity at $T_g$ or simply heat capacity change at $T_g$, $\Delta C_p(T_g)$, shows a relatively good correlation with the configurational entropy and physical stability. Hence $\Delta C_p(T_g)$ which can be obtained from a conventional DSC measurement, may serve as an approximate indicator or surrogate for configurational entropy. Heat capacity is a direct measurement on the modes by which a molecule can dissipate heat energies therefore is a physically meaningful measure of configurations. The heat capacity change at the glass transition temperature directly reflects the number of configurations that become available as a result of the glass-supercooled liquid transition. Because the temperature range of typical glass transition is relatively small, the contribution of anharmonic vibrations may be minimal. Therefore, such practices minimize the concerns on the true configurational origin of the excess entropy obtained via thermal analysis.

In addition, $\Delta C_p(T_g)$ can be used to estimate the strength parameter D for a glass based on the Adam-Gibbs model and the assumption of hyperbolic temperature relationship of the configurational heat capacity, $C_{p\,conf}$ at temperatures above $T_g$:

$$K = T \cdot C_{p\,conf} \approx T_g \cdot \Delta C_p(T_g)$$

The entropy-based Kauzmann temperature is calculated as:

$$T_0 = \frac{T_m}{1 + \Delta H_m/K}$$

where $T_m$ and $\Delta H_m$ are the temperature and enthalpy of melting, respectively. Hence the strength parameter may be derived as:

$$D = \frac{T_g - T_0}{T_0} \cdot \ln(\tau_g/\tau_0)$$

The advantage of using $\Delta C_p(T_g)$ as an estimate of configurational entropy is that this quantity can be readily measured without laborious procedures such as those required for the determination of configuration entropy. In addition, the configurational entropy at $T_g$ may be estimated based on $\Delta C_p(T_g)$ and other relevant parameters:

$$S_{conf}(T_g) = \Delta S_m - \int_{T_g}^{T_m} \frac{C_{p\,conf}}{T}\, dT \approx \Delta S_m - K\left(\frac{1}{T_g} - \frac{1}{T_m}\right)$$

where $\Delta S_m$ is the entropy of melting.

The strength parameter D can therefore be used to represent the molecular mobility of an amorphous material, and the configurational entropy can be represented by its quantity at the glass transition temperature, or more conveniently, it can be represented by the change in heat capacity at $T_g$, $\Delta C_p(T_g)$. The high-low criterion for each quantity can then be defined to be used in the ACS assignment.

The criterion for stability is different across different fields of applications. Pharmaceutical products often concern the stability during the typical shelf lives, e.g., 2-3 years. A benchmarking approach may be adopted by surveying a number of pharmaceutical compounds with known physical stability, including those whose ASD formulations have been successfully commercialized. These compounds encompass a wide variety of structural features and a broad spectrum ranging from rapid crystallizers (such as acetaminophen, griseofulvin, phenobarbital, and sulfathiazole) to some that form kinetically stable amorphous phases (such as itraconazole, ketoconazole, saquinavir, ritonavir and lopinavir). These compounds include ritonavir, acetaminophen, fenofibrate, sucrose, nifedipine, griseofulvin, lopinavir, lovastatin, felodipine, indomethacin, itraconazole, ketoconazole, phenobarbital, flopropione, celecoxib, etoricoxib, rofecoxib, Valdecoxib, tolbutamide, quinidine, phenylbutazone, sulfathiazole, hydrochlorthiazide, glibenclamide, cimetidine, atropine, rac-Ibuprofen, salicin, santonin, simvastatin, and saquinavir.

Based on the assessments of mobility and configurational entropy, and the known physical stability for the above selected compounds in their amorphous states, the following criteria was developed:

(1) D≥9 as the high molecular mobility criterion;
(2) $S_{conf}(T_g)R \geq 6$ as the criterion for high configurational entropy. Alternatively high configurational entropy may be considered when $\Delta C_p(T_g)/R \geq 23$.

Choices of these criteria allow for categorization of the compounds into four categories in the context of physical stability or crystallization tendency. In many times, the configurational features of each molecule are reflected consistently by the simple measurement of $\Delta C_p(T_g)$ and information can be conveniently extracted to allow the ACS determination. The use of $\Delta C_p(T_g)$ allows the ACS assignment of a molecule even when no crystal form is identified, provided that the molecular mobility can be evaluated independently by other means such as viscosity measurement and the scanning rate dependence of the glass transition temperature.

Based on the above-described ACS model, it is believed that a selected HCV inhibitor described hereinabove is a good candidate for developing ASD formulations.

In one aspect, the present invention features a solid composition comprising (1) a selected HCV inhibitor, (2) a pharmaceutically acceptable hydrophilic polymer, and optionally (3) a pharmaceutically acceptable surfactant, wherein the selected HCV inhibitor is telaprevir (VX-950), BI-201335, TMC-435 (TMC-435350), vaniprevir (MK-7009), MK-5172, asunaprevir (BMS-650032), daclatasvir (BMS-790052), danoprevir, setrobuvir (ANA-598), tegobuvir (GS-333126 or GS-9190), GS-9451, mericitabine (R-4048), IDX-184, filibuvir (PF-00868554), PSI-7977, PSI-352938, BIT-225, boceprevir, GS-5885 or GS-9256. The selected HCV inhibitor and the polymer can be formulated in a solid dispersion. The surfactant may be formulated in the same solid dispersion; or the surfactant can be separately combined or mixed with the solid dispersion.

In one embodiment, a solid composition of the invention comprises an amorphous solid dispersion which comprises (1) the selected HCV inhibitor, (2) a pharmaceutically acceptable hydrophilic polymer, and (3) a pharmaceutically acceptable surfactant. In another embodiment, a solid composition of the invention comprises a solid solution which comprises (1) the selected HCV inhibitor, and (2) a pharmaceutically acceptable hydrophilic polymer. In still another embodiment, a solid composition of the invention comprises a solid solution which comprises (1) the selected HCV inhibitor, (2) a pharmaceutically acceptable hydrophilic polymer, and (3) a pharmaceutically acceptable surfactant. In yet another embodiment, a solid composition of the invention comprises a glassy solution which includes (1) the selected HCV inhibitor, and (2) a pharmaceutically acceptable hydrophilic polymer. In a further embodiment, a solid composition of the invention comprises a glassy solution which includes (1) the selected HCV inhibitor, (2) a pharmaceutically acceptable hydrophilic polymer, and (3) a pharmaceutically acceptable surfactant.

A solid composition (or a solid dispersion) of the invention can contain, for example, at least 1% by weight of the selected HCV inhibitor, preferably at least 5%, including, e.g., at least 10%. For instance, a solid composition (or a solid dispersion) of the invention can contain from 1 to 50% by weight of the selected HCV inhibitor. For another instance, a solid composition (or a solid dispersion) of the invention can contain from 5 to 30% by weight of the selected HCV inhibitor. Preferably, a solid composition (or a solid dispersion) of the invention contains from 5 to 15% by weight of the selected HCV inhibitor.

A solid dispersion of the invention may contain at least 30% by weight of a pharmaceutically acceptable hydrophilic polymer or a combination of such hydrophilic polymers. Preferably, the solid dispersion contains at least 40% by weight of a pharmaceutically acceptable hydrophilic polymer or a combination of such hydrophilic polymers. More preferably, the solid dispersion contains at least 50% (including, e.g., at least 60%, 70%, 80% or 90%) by weight of a pharmaceutically acceptable hydrophilic polymer or a combination of such polymers. A solid dispersion (or a solid composition) of the invention may also contain at least 1% by weight of a pharmaceutically acceptable surfactant or a combination of such surfactants. Preferably, the solid dispersion (or solid composition) contains at least 2% by weight of a pharmaceutically acceptable surfactant or a combination of such surfactants. More preferably, the solid dispersion (or solid composition) contains from 4% to 20% by weight of the surfactant(s), such as from 5% to 10% by weight of the surfactant(s).

In one embodiment, a solid dispersion (or a solid composition) of the invention comprises at least 30% by weight of a pharmaceutically acceptable hydrophilic polymer or a combination of such polymers, and at least 1% by weight of a pharmaceutically acceptable surfactant or a combination of such surfactants. In another embodiment, a solid dispersion (or a solid composition) of the invention comprises at least 50% by weight of a pharmaceutically acceptable hydrophilic polymer or a combination of such polymers, and from 2% to 20% by weight of a pharmaceutically acceptable surfactant or a combination of such surfactants. In yet another embodiment, a solid dispersion (or a solid composition) of the invention comprises from 50% to 90% by weight of a pharmaceutically acceptable hydrophilic polymer or a combination of such polymers, and from 3% to 15% by weight of a pharmaceutically acceptable surfactant or a combination of such surfactants. In yet another embodiment, a solid dispersion (or a solid composition) of the invention comprises from 70% to 90% by weight of a pharmaceutically acceptable hydrophilic polymer or a combination of such polymers, and from 5% to 10% by weight of a pharmaceutically acceptable surfactant or a combination of such surfactants.

Preferably, a hydrophilic polymer employed in the present invention has a $T_g$ of at least 50° C., more preferably at least 60° C., and highly preferably at least 80° C. including, but not limited to from, 80° C. to 180° C., or from 100° C. to 150° C. Methods for determining $T_g$ values of organic polymers are described in INTRODUCTION TO PHYSICAL POLYMER SCIENCE (2nd Edition by L. H. Sperling, published by John Wiley & Sons, Inc., 1992). The $T_g$ value can be calculated as the weighted sum of the $T_g$ values for homopolymers derived from each of the individual monomers, i.e., the polymer $T_g = \Sigma W_i \cdot X_i$ where $W_i$ is the weight percent of monomer in the organic polymer, and $X_i$ is the $T_g$ value for the homopolymer derived from monomer i. $T_g$ values for the homopolymers may be taken from POLYMER HANDBOOK (2nd Edition by J. Brandrup and E. H. Immergut, Editors, published by John Wiley & Sons, Inc., 1975). Hydrophilic polymers with a $T_g$ as described above may allow for the preparation of solid dispersions that are mechanically stable and, within ordinary temperature ranges, sufficiently temperature stable so that the solid dispersions may be used as dosage forms without further processing or be compacted to tablets with only a small amount of tabletting aids. Hydrophilic polymers having a $T_g$ of below 50° C. may also be used.

Preferably, a hydrophilic polymer employed in the present invention is water-soluble. A solid composition of the present invention can also comprise poorly water-soluble or water-insoluble polymer or polymers, such as cross-linked polymers. A hydrophilic polymer comprised in a solid composition of the present invention preferably has an apparent viscosity, when dissolved at 20° C. in an aqueous solution at 2% (w/v), of 1 to 5000 mPa·s., and more preferably of 1 to 700 mPa·s, and most preferably of 5 to 100 mPa·s.

Hydrophilic polymers suitable for use in a solid composition of the invention include, but are not limited to, homopolymers or copolymers of N-vinyl lactams, such as homopolymers or copolymers of N-vinyl pyrrolidone (e.g., polyvinylpyrrolidone (PVP), or copolymers of N-vinyl pyrrolidone and vinyl acetate or vinyl propionate); cellulose esters or cellulose ethers, such as alkylcelluloses (e.g., methylcellulose or ethylcellulose), hydroxyalkylcelluloses (e.g., hydroxypropylcellulose), hydroxyalkylalkylcelluloses (e.g., hydroxypropylmethylcellulose), and cellulose phthalates or succinates (e.g., cellulose acetate phthalate and hydroxypropylmethylcellulose phthalate, hydroxypropylmethylcellulose succinate, or hydroxypropylmethylcellulose acetate succinate); high molecular polyalkylene oxides, such as polyethylene oxide, polypropylene oxide, and copolymers of ethylene oxide and propylene oxide; polyacrylates or polymethacrylates, such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), and poly(hydroxyalkyl methacrylates); polyacrylamides; vinyl acetate polymers, such as copolymers of vinyl acetate and crotonic acid, and partially hydrolyzed polyvinyl acetate (also referred to as partially saponified "polyvinyl alcohol"); polyvinyl alcohol; oligo- or polysaccharides, such as carrageenans, galactomannans, and xanthan gum; polyhydroxyalkylacrylates; polyhydroxyalkyl-methacrylates; copolymers of methyl methacrylate and acrylic acid; polyethylene glycols (PEGs); graft copolymers of polyethylene glycol/polyvinyl caprolactam/polyvinyl acetate, or any mixture or combination thereof. In some cases, sugar alcohols can be used in addition to, or in lieu of, hydrophilic polymers.

Non-limiting examples of preferred hydrophilic polymers for the invention include polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, Soluplus, poloxamer 124, poloxamer 188, poloxamer 237, poloxamer 338, and poloxamer 407.

Of these, homopolymers or copolymers of N-vinyl pyrrolidone, such as copolymers of N-vinyl pyrrolidone and vinyl acetate, are preferred. A non-limiting example of a preferred polymer is a copolymer of 60% by weight of N-vinyl pyrrolidone and 40% by weight of vinyl acetate. Other preferred polymers include, without limitation, hydroxypropyl methylcellulose (HPMC, also known as hypromellose in USP), such as hydroxypropyl methylcellulose grade E5 (HPMC-E5); and hydroxypropyl methylcellulose acetate succinate (HPMC-AS).

A pharmaceutically acceptable surfactant employed in the present invention is preferably a non-ionic surfactant. Ionic surfactants may also be used. More preferably, a solid composition of the present invention comprises a pharmaceutically acceptable surfactant having an HLB value of from 2-20. In one example, a solid composition of the present invention includes a mixture of pharmaceutically acceptable surfactants, with at least one surfactant having an HLB value of no less than 10 and at least another surfactant having an HLB value of below 10. The HLB system (Fiedler, H. B., ENCYCLOPEDIA OF EXCIPIENTS, 5$^{th}$ ed., Aulendorf: ECV-Editio-Cantor-Verlag (2002)) attributes numeric values to surfactants, with lipophilic substances receiving lower HLB values and hydrophilic substances receiving higher HLB values.

Non-limiting examples of pharmaceutically acceptable surfactants that are suitable for the present invention include polyoxyethylene castor oil derivates, e.g. polyoxyethyleneglycerol triricinoleate or polyoxyl 35 castor oil (Cremophor EL; BASF Corp.) or polyoxyethyleneglycerol oxystearate such as polyethylenglycol 40 hydrogenated castor oil (Cremophor RH 40, also known as polyoxyl 40 hydrogenated castor oil or macrogolglycerol hydroxystearate) or polyethylenglycol 60 hydrogenated castor oil (Cremophor RH 60); or a mono fatty acid ester of polyoxyethylene sorbitan, such as a mono fatty acid ester of polyoxyethylene (20) sorbitan, e.g. polyoxyethylene (20) sorbitan monooleate (Tween 80), polyoxyethylene (20) sorbitan monostearate (Tween 60), polyoxyethylene (20) sorbitan monopalmitate (Tween 40), or polyoxyethylene (20) sorbitan monolaurate (Tween 20). Other non-limiting examples of suitable surfactants include polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (lauroglycol, such as lauroglycol FCC); sucrose fatty acid esters, e.g. sucrose monostearate, sucrose distearate, sucrose monolaurate, sucrose dilaurate; sorbitan fatty acid mono esters such as sorbitan mono laurate (Span 20), sorbitan monooleate, sorbitan monopalnitate (Span 40), or sorbitan stearate; D-alpha-tocopheryl polyethylene glycol 1000 succinate; or a combination or mixture thereof. Other suitable surfactants include, but are not limited to, block copolymers of ethylene oxide and propylene oxide, also known as polyoxyethylene polyoxypropylene block copolymers or polyoxyethylene polypropyleneglycol, such as Poloxamer 124, Poloxamer 188, Poloxamer 237, Poloxamer 388, or Poloxamer 407 (BASF Wyandotte Corp.). As described above, a mixture of surfactants can be used in a solid composition of the present invention.

Non-limiting examples of preferred surfactants for the invention include to polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, and sorbitan monolaurate.

In one embodiment, a solid composition of the present invention comprises an amorphous solid dispersion or solid solution which includes (1) a selected HCV inhibitor selected from telaprevir (VX-950), BI-201335, TMC-435 (TMC-435350), vaniprevir (MK-7009), MK-5172, asunaprevir (BMS-650032), daclatasvir (BMS-790052), danoprevir, setrobuvir (ANA-598), tegobuvir (GS-333126 or GS-9190), GS-9451, mericitabine (R-4048), IDX-184, filibuvir (PF-00868554), PSI-7977, PSI-352938, BIT-225, boceprevir, GS-5885 or GS-9256, and (2) a pharmaceutically acceptable hydrophilic polymer. The solid composition can also include a pharmaceutically acceptable surfactant which preferably is formulated in the amorphous solid dispersion or solid solution. The hydrophilic polymer can be selected, for example, from the group consisting of homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, and polysaccharide. As a non-limiting example, the hydrophilic polymer is selected from the group consisting of homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, graft copolymer of polyethylene glycol/polyvinyl caprolactam/polyvinyl acetate, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, and xanthan gum. Preferably, the hydrophilic polymer is selected from polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, Soluplus, poloxamer 124, poloxamer 188, poloxamer 237, poloxamer 338, or poloxamer 407. More preferably, the hydrophilic polymer is selected from homopolymers of vinylpyrrolidone (e.g., PVP with Fikentscher K values of from 12 to 100, or PVP with Fikentscher K values of from 17 to 30), or copolymers of 30 to 70% by weight of N-vinylpyrrolidone (VP) and 70 to 30% by weight of vinyl acetate (VA) (e.g., a copolymer of 60% by weight VP and 40% by weight VA). The surfactant can be selected, for example, from the group consisting of polyoxyethyleneglycerol triricinoleate or polyoxyl 35 castor oil (Cremophor EL; BASF Corp.) or polyoxyethyleneglycerol oxystearate, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, and sorbitan fatty acid mono ester. As a non-limited example, the surfactant is selected from the group consisting of polyethylenglycol 40 hydrogenated castor oil (Cremophor RH 40, also known as polyoxyl 40 hydrogenated castor oil or macrogolglycerol hydroxystearate), polyethylenglycol 60 hydrogenated castor oil (Cremophor RH 60), a mono fatty acid ester of polyoxyethylene (20) sorbitan (e.g. polyoxyethylene (20) sorbitan monooleate (Tween 80), polyoxyethylene (20) sorbitan monostearate (Tween 60), polyoxyethylene (20) sorbitan monopalmitate (Tween 40), or polyoxyethylene (20) sorbitan monolaurate (Tween 20)), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate, D-alpha-tocopheryl polyethylene glycol 1000 succinate, sucrose monostearate, sucrose distearate, sucrose monolaurate, sucrose dilaurate, sorbitan monolaurate, sorbitan monooleate, sorbitan monopalnitate, and sorbitan stearate. Preferably, the surfactant is selected from polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, or sorbitan monolaurate. More preferably, the surfactant is selected from sorbitan monolaurate, D-alpha-tocopheryl polyethylene glycol 1000 succinate, propylene glycol monolaurate, or a combination thereof (e.g., a combination of D-alpha-tocopheryl polyethylene glycol 1000 succinate and lauroglycol FCC).

In another embodiment, a solid composition of the present invention comprises an amorphous solid dispersion or solid solution which includes (1) a selected HCV inhibitor described hereinabove, and (2) a homopolymer or copolymer of N-vinyl pyrrolidone (e.g., copovidone). The solid composition also comprises a pharmaceutically acceptable surfactant (e.g., vitamin E TPGS, sorbitan monolaurate, or a combination of vitamin E TPGS and lauroglycol FCC), wherein the surfactant preferably is formulated in the amorphous solid dispersion or solid solution.

In yet another embodiment, a solid composition of the present invention comprises an amorphous solid dispersion or solid solution which includes (1) a selected HCV inhibitor described hereinabove, (2) copovidone, and (3) a pharmaceutically acceptable surfactant (e.g., vitamin E TPGS, sorbitan monolaurate, or a combination of vitamin E TPGS and lauroglycol FCC). The amorphous solid dispersion or solid solution may also include another pharmaceutically acceptable surfactant.

In still another embodiment, a solid composition of the present invention comprises an amorphous solid dispersion or solid solution which includes (1) 10% by weight the selected HCV inhibitor, (2) 82% by weight copovidone, and (3) 5% by weight vitamin E TPGS and 2% by weight lauroglycol FCC. The solid composition can also include 1% by weight colloidal silica.

In a further embodiment, a solid composition of the present invention comprises an amorphous solid dispersion or solid solution which includes (1) 10% by weight the selected HCV inhibitor, (2) 82% by weight copovidone, and (3) 7% by weight propylene glycol monocaprylate (Capryol 90). The solid composition can also include 1% by weight colloidal silica.

A solid dispersion employed in the present invention preferably comprises or consists of a single-phase (defined in thermodynamics) in which the therapeutic agent(s) (e.g., a selected HCV inhibitor described hereinabove with or without another anti-HCV agent) is molecularly dispersed in a matrix containing the pharmaceutically acceptable hydrophilic polymer(s). In such cases, thermal analysis of the solid dispersion using differential scanning calorimetry (DSC) typically shows only one single $T_g$, and the solid dispersion does not contain any detectable crystalline HCV inhibitor as measured by X-ray powder diffraction spectroscopy.

A solid composition of the present invention can further include one or more other anti-HCV agents. These other anti-HCV agents can be, for example, HCV polymerase inhibitors (including nucleoside or non-nucleoside type of polymerase inhibitors), HCV protease inhibitors, HCV helicase inhibitors, CD81 inhibitors, cyclophilin inhibitors, internal ribosome entry site inhibitors, or HCV NS5A inhibitors.

In one embodiment, a solid composition of the invention comprises (1) a selected HCV inhibitor described hereinabove and (2) another HCV protease inhibitor. In another embodiment, a solid composition of the invention comprises (1) a selected HCV inhibitor described hereinabove, and (2) another HCV polymerase inhibitor (e.g., a non-nucleoside polymerase inhibitor, or preferably a nucleoside polymerase inhibitor). In yet another embodiment, a solid composition of the invention comprises (1) a selected HCV inhibitor described hereinabove, (2) another HCV protease inhibitor, and (3) another HCV polymerase inhibitor (e.g., a non-nucleoside polymerase inhibitor, or preferably a nucleoside polymerase inhibitor). In another embodiment, a solid composition of the invention comprises (1) a selected HCV inhibitor described hereinabove, and (2) another HCV NS5A inhibitor. In another embodiment, a solid composition of the invention comprises (1) a selected HCV inhibitor described hereinabove, (2) another HCV polymerase inhibitor (e.g., a non-nucleoside polymerase inhibitor, or preferably a nucleoside polymerase inhibitor), and (3) another HCV NS5A inhibitor. In another embodiment, a solid composition of the invention comprises (1) a selected HCV inhibitor described hereinabove, (2) another HCV protease inhibitor, and (3) another HCV NS5A inhibitor.

Non-limiting examples of other protease inhibitors can be selected from ACH-1095 (Achillion), ACH-1625 (Achillion), ACH-2684 (Achillion), AVL-181 (Avila), AVL-192 (Avila), BI-201335 (Boehringer Ingelheim), BMS-650032 (BMS), boceprevir, danoprevir, GS-9132 (Gilead), GS-9256 (Gilead), GS-9451 (Gilead), IDX-136 (Idenix), IDX-316 (Idenix), IDX-320 (Idenix), MK-5172 (Merck), narlaprevir, PHX-1766 (Phenomix), telaprevir, TMC-435 (Tibotec), vaniprevir, VBY708 (Virobay), VX-500 (Vertex), VX-813 (Vertex), VX-985 (Vertex), or a combination thereof. And non-limiting examples of other HCV polymerase inhibitors can be selected from ABT-072 (Abbott), ABT-333 (Abbott), ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-222 (VCH-222) (Vertex & ViraChem), VX-759 (Vertex), GS-6620 (Gilead), IDX-102 (Idenix), IDX-184 (Idenix), INX-189 (Inhibitex), MK-0608 (Merck), PSI-7977 (Pharmasset), PSI-938 (Pharmasset), RG7128 (Roche), TMC64912 (Medivir), GSK625433 (GlaxoSmithKline), BCX-4678 (BioCryst), or a combination thereof. The polymerase inhibitor may be a nucleotide polymerase inhibitor, such as GS-6620 (Gilead), IDX-102 (Idenix), IDX-184 (Idenix), INX-189 (Inhibitex), MK-0608 (Merck), PSI-7977 (Pharmasset), PSI-938 (Pharmasset), RG7128 (Roche), TMC64912 (Medivir), or a combination thereof. The polymerase inhibitor may also be a non-nucleoside polymerase inhibitor, such as ABT-072 (Abbott), ABT-333 (Abbott), ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-222 (VCH-222) (Vertex & ViraChem), VX-759 (Vertex), or a combination thereof. The present invention also contemplates the inclusion of both a nucleotide polymerase inhibitor and a non-nucleoside polymerase inhibitor in a solid composition of the invention. Non-limiting examples of other HCV NS5A inhibitors include ACH-2928 (Achillion), AZD2836 (Astra-Zeneca), AZD7295 (Astra-Zeneca), BMS-790052 (BMS), BMS-824393 (BMS), EDP-239 (Enanta), GS-5885 (Gilead), PPI-1301 (Presidio), PPI-461 (Presidio), GSK62336805, or a combination thereof.

A solid composition of the present invention preferably is a solid oral dosage form. Common solid oral dosage forms suitable for the present invention include, but are not limited to, capsules, dragees, granules, pills, powders and tablets, with capsules and tablets being preferred. A solid oral dosage form of the present invention can also include other excipients or inset diluents, such as sucrose, lactose or starch. Lubricants, coloring agents, releasing agents, coating agents, sweetening or flavoring agents, buffering agents, preservatives, or antioxidants can also be included in a solid oral dosage form of the present invention.

A solid composition of the present invention can be prepared by a variety of techniques such as, without limitation, melt-extrusion, spray-drying, co-precipitation, freeze drying, or other solvent evaporation techniques, with melt-extrusion and spray-drying being preferred. The melt-extrusion process typically comprises the steps of preparing a melt which includes the active ingredient(s), the hydrophilic polymer(s) and preferably the surfactant(s), and then cooling the melt until it solidifies. Melting often involves a transition into a liquid state in which it is possible for one component to get dissolved or embedded, preferably homogeneously dissolved or embedded, in the other component or components. In many cases, the polymer component(s) will melt and the other components including the active ingredient(s) and surfactant(s) will dissolve in the melt thereby forming a solution. In such a case, the polymer functions as a solvent. Melting usually involves heating above the softening point of the polymer(s). The preparation of the melt can take place in a variety of ways. The mixing of the components can take place before, during or after the formation of the melt. For example, the components can be mixed first and then melted or be simultaneously mixed and melted. The melt can also be homogenized in order to disperse the active ingredient(s) efficiently. In addition, it may be convenient first to melt the polymer(s) and then to mix in and homogenize the active ingredient(s). In one example, all materials except surfactant(s) are blended and fed into an extruder, while the surfactant(s) is molten externally and pumped in during extrusion.

In another example, the melt comprises a selected HCV inhibitor described hereinabove, and one or more hydrophilic polymers described above; and the melt temperature is in the range of from 100 to 170° C., preferably from 120 to 150° C., and highly preferably from 135 to 140° C. The melt can also include a pharmaceutically acceptable surfactant described above.

In still another example, the melt comprises a selected HCV inhibitor described hereinabove, at least another anti-HCV agent described above, and one or more hydrophilic polymers described above. The melt can also include a pharmaceutically acceptable surfactant described above.

To start a melt-extrusion process, the active ingredient(s) (e.g., a selected HCV inhibitor described hereinabove) can be employed in their solid forms, such as their respective crystalline forms. The active ingredient(s) can also be employed as a solution or dispersion in a suitable liquid solvent such as alcohols, aliphatic hydrocarbons, esters or, in some cases, liquid carbon dioxide. The solvent can be removed, e.g. evaporated, upon preparation of the melt.

Various additives can also be included in the melt, for example, flow regulators (e.g., colloidal silica), binders, lubricants, fillers, disintegrants, plasticizers, colorants, or stabilizers (e.g., antioxidants, light stabilizers, radical scavengers, and stabilizers against microbial attack).

The melting and/or mixing can take place in an apparatus customary for this purpose. Particularly suitable ones are extruders or kneaders. Suitable extruders include single screw extruders, intermeshing screw extruders or multiscrew extruders, preferably twin screw extruders, which can be corotating or counterrotating and, optionally, be equipped with kneading disks. It will be appreciated that the working temperatures will be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt can range from thin to pasty to viscous. Shaping of the extrudate can be conveniently carried out by a calender with two counter-rotating rollers with mutually matching depressions on their surface. The extrudate can be cooled and allow to solidify. The extrudate can also be cut into pieces, either before (hot-cut) or after solidification (cold-cut).

The solidified extrusion product can be further milled, ground or otherwise reduced to granules. The solidified extrudate, as well as each granule produced, comprises a solid dispersion, preferably a solid solution, of the active ingredient(s) in a matrix comprised of the hydrophilic polymer(s) and optionally the pharmaceutically acceptable surfactant(s). Where the granules do not contain any surfactant, a pharmaceutically acceptable surfactant described above can be added to and blended with the granules. The extrusion product can also be blended with other active ingredient(s) and/or additive(s) before being milled or ground to granules. The granules can be further processed into suitable solid oral dosage forms.

In some cases, direct-shaping techniques such as injection moulding can be used in combination with melt extrusion to prepare suitable solid dosage forms.

In one example, copovidone and one or more surfactants are mixed and granulated, followed by the addition of aerosil and a selected HCV inhibitor described hereinabove. The mixture, which may contain for example at least 5% by weight of the selected HCV inhibitor is then milled. The mixture is then subject to extrusion, and the extrudate thus produced can be milled and sieved for further processing to make capsules or tablets. Surfactant(s) employed in this example can also be added through liquid dosing during extrusion.

The approach of solvent evaporation, via spray-drying, provides the advantage of allowing for processability at lower temperatures, if needed, and allows for other modifications to the process in order to further improve powder properties. The spray-dried powder can then be formulated further, if needed, and final drug product is flexible with regards to whether capsule, tablet or any other solid dosage form is desired.

Exemplary spray-drying processes and spray-drying equipment are described in K. Masters, SPRAY DRYING HANDBOOK (Halstead Press, New York, 4$^{th}$ ed., 1985). Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus. This help to ensure that the dried droplets are essentially solid and can form a fine powder and do not stick to the apparatus wall. The spray-dried product can be collected by removing the material manually, pneumatically, mechanically or by other suitable means. The actual length of time to achieve the preferred level of dryness depends on the size of the droplets, the formulation, and spray dryer operation. Following the solidification, the solid powder may stay in the spray drying chamber for additional time (e.g., 5-60 seconds) to further evaporate solvent from the solid powder. The final solvent content in the solid dispersion as it exits the dryer is preferably at a sufficiently low level so as to improve the stability of the final product. For instance, the residual solvent content of the spray-dried powder can be less than 2% by weight. Highly preferably, the residual solvent content is within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other processes.

Like the solid extrudate described above, the spray dried product contains a solid dispersion, preferably a solid solution, of the active ingredient(s) in a matrix comprised of the hydrophilic polymer(s) and optionally the pharmaceutically acceptable surfactant(s). Where the spray dried product does not contain any surfactant, a pharmaceutically acceptable surfactant described above can be added to and blended with the spray-dried product before further processing.

Before feeding into a spray dryer, the active ingredient(s) (e.g., a selected HCV inhibitor described hereinabove), the hydrophilic polymer(s), as well as other optional active ingredients or excipients such as the pharmaceutically acceptable surfactant(s), can be dissolved in a solvent. Suitable solvents include, but are not limited to, water, alkanols (e.g., methanol, ethanol, 1-propanol, 2-propanol or mixtures thereof), acetone, acetone/water, alkanol/water mixtures (e.g., ethanol/water mixtures), or combinations thereof. The solution can also be preheated before being fed into the spray dryer.

The solid dispersion produced by melt-extrusion, spray-drying or other techniques can be prepared into any suitable solid oral dosage forms. In one embodiment, the solid dispersion prepared by melt-extrusion, spray-drying or other techniques (e.g., the extrudate or the spray-dried powder) can be compressed into tablets. The solid dispersion can be either directly compressed, or milled or ground to granules or powders before compression. Compression can be done in a tablet press, such as in a steel die between two moving punches. When a solid composition of the present invention comprises a selected HCV inhibitor described hereinabove and another anti-HCV agent, it is possible to separately prepare solid dispersions of each individual active ingredient and then blend the optionally milled or ground solid dispersions before compacting. A selected HCV inhibitor described hereinabove and other active ingredient(s) can also be prepared in the same solid dispersion, optionally milled and/or blended with other additives, and then compressed into tablets.

At least one additive selected from flow regulators, binders, lubricants, fillers, disintegrants, or plasticizers may be used in compressing the solid dispersion. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like.

Various other additives may also be used in preparing a solid composition of the present invention, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack.

Solid compositions according to certain embodiments of the present invention may contain several layers, for example laminated or multilayer tablets. They can be in open or closed form. "Closed dosage forms" are those in which one layer is completely surrounded by at least one other layer.

In order to facilitate the intake of a solid dosage form, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. The film-coat usually includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. polysorbates, and optionally a pigment, e.g. titanium dioxide or iron oxides. The film-coating may also comprise talc as anti-adhesive. Preferably, the film coat accounts for less than 5% by weight of a pharmaceutical composition of the present invention.

In another aspect, the present invention feature methods of using solid compositions of the present invention to treat HIV infection. The methods comprise administering a solid composition of the present invention to a patient in need thereof. A solid composition of the present invention can be administered either alone, or in combination with one or more other anti-HCV agents, such as those described hereinabove. The specific inhibitory dose for any particular patient will depend upon a variety of factors including the severity of the HCV infection; the activity of the active ingredient(s) in the particular patient; the specific solid composition employed; the age, body weight, general health, sex and diet of the patient; the time of administration and rate of excretion; the duration of the treatment; drugs used in combination or coincidental with the selected HCV inhibitor described hereinabove; and like factors well known in the medical arts.

In one embodiment, a method of the present invention comprises administering to a patient in need thereof a solid composition of the present invention and at least another anti-HCV agent, wherein said another anti-HCV agent is selected from HCV polymerase inhibitors (e.g., nucleoside or non-nucleoside HCV polymerase inhibitors), HCV protease inhibitors, HCV helicase inhibitors, CD81 inhibitors, cyclophilin inhibitors, internal ribosome entry site inhibitors, or HCV NS5A inhibitors. Preferably, said another anti-HCV agent is an HCV polymerase inhibitor (e.g., nucleoside or non-nucleoside HCV polymerase inhibitor) or an HCV protease inhibitor. Also preferably, said another anti-HCV agent is interferon or ribavirin, or preferably a combination thereof. The interferon preferably is α-interferon, and more preferably, pegylated interferon-α such as PEGASYS (peginterferon alfa-2a). The administration of a solid composition of the present invention and another anti-HCV agent(s) can be concurrent or sequential.

The present invention also features use of a solid composition of the present invention for the manufacture of medicaments for the treatment of HCV infection.

In one embodiment, the selected HCV inhibitor used in any aspect, embodiment, example or feature described hereinabove is telaprevir (VX-950).

In another embodiment, the selected HCV inhibitor used in any aspect, embodiment, example or feature described hereinabove is BI-201335.

In another embodiment, the selected HCV inhibitor used in any aspect, embodiment, example or feature described hereinabove is TMC-435 (TMC-435350).

In another embodiment, the selected HCV inhibitor used in any aspect, embodiment, example or feature described hereinabove is vaniprevir (MK-7009).

In another embodiment, the selected HCV inhibitor used in any aspect, embodiment, example or feature described hereinabove is MK-5172.

In another embodiment, the selected HCV inhibitor used in any aspect, embodiment, example or feature described hereinabove is asunaprevir (BMS-650032).

In another embodiment, the selected HCV inhibitor used in any aspect, embodiment, example or feature described hereinabove is daclatasvir (BMS-790052).

In another embodiment, the selected HCV inhibitor used in any aspect, embodiment, example or feature described hereinabove is danoprevir. Preferably, danoprevir is used together with ritonavir to improve the pharmacokinetics of danoprevir. More preferably, danoprevir is co-formulated with ritonavir in a solid composition of the invention. For instance, danoprevir and ritonavir in a solid composition of the invention can be formulated in the same solid dispersion or different solid dispersions.

In another embodiment, the selected HCV inhibitor used in any aspect, embodiment, example or feature described hereinabove is setrobuvir (ANA-598).

In another embodiment, the selected HCV inhibitor used in any aspect, embodiment, example or feature described hereinabove is tegobuvir (GS-333126 or GS-9190). Preferably, a solid composition of this embodiment further comprises GS-9256, GS-9451 or GS-5885. Also preferably, a solid composition of this embodiment further comprises GS-9451 and GS-5885.

In another embodiment, the selected HCV inhibitor used in any aspect, embodiment, example or feature described hereinabove is GS-9451. Preferably, a solid composition of this embodiment further comprises tegobuvir or GS-5885. Also preferably, a solid composition of this embodiment further comprises tegobuvir and GS-5885.

In another embodiment, the selected HCV inhibitor used in any aspect, embodiment, example or feature described hereinabove is mericitabine (R-4048).

In another embodiment, the selected HCV inhibitor used in any aspect, embodiment, example or feature described hereinabove is IDX-184.

In another embodiment, the selected HCV inhibitor used in any aspect, embodiment, example or feature described hereinabove is filibuvir (PF-00868554).

In another embodiment, the selected HCV inhibitor used in any aspect, embodiment, example or feature described hereinabove is PSI-7977. Preferably, a solid composition of this embodiment further comprises GS-5885 or daclatasvir.

In another embodiment, the selected HCV inhibitor used in any aspect, embodiment, example or feature described hereinabove is PSI-352938.

In another embodiment, the selected HCV inhibitor used in any aspect, embodiment, example or feature described hereinabove is BIT-225.

In another embodiment, the selected HCV inhibitor used in any aspect, embodiment, example or feature described hereinabove is boceprevir.

In another embodiment, the selected HCV inhibitor used in any aspect, embodiment, example or feature described hereinabove is GS-5885. Preferably, a solid composition of this embodiment further comprises PSI-7977, GS-9451 or tegobuvir. Also preferably, a solid composition of this embodiment further comprises GS-9451 and tegobuvir. In one example, a solid oral dosage form of the invention comprises an amorphous solid dispersion, wherein said solid dispersion comprises GS-5885, copovidone and optionally a pharmaceutically acceptable surfactant. In another example, a solid oral dosage form of the invention comprises an amorphous solid dispersion, wherein said solid dispersion comprises GS-5885, copovidone and optionally a pharmaceutically acceptable surfactant, and wherein said solid oral dosage form further comprises

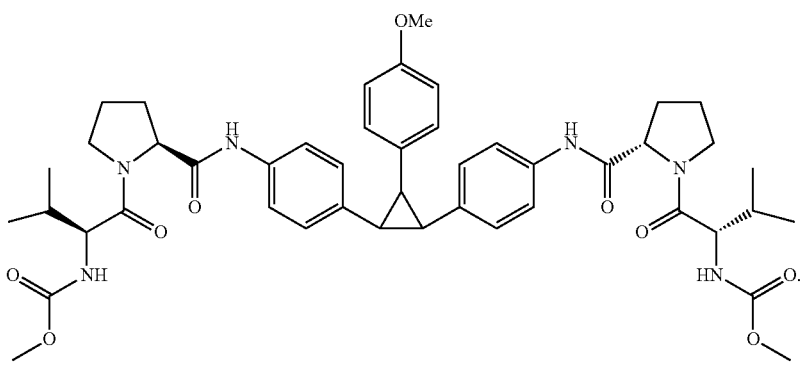 [SMILES: COC(=O)N[C@H](C(=O)N1CCC[C@H]1C(=O)Nc1ccc(C2C(c3ccc(NC(=O)[C@@H]4CCCN4C(=O)[C@@H](NC(=O)OC)C(C)C)cc3)C2c2ccc(OC)cc2)cc1)C(C)C]

In another embodiment, the selected HCV inhibitor used in any aspect, embodiment, example or feature described hereinabove is GS-9256. Preferably, a solid composition of this embodiment further comprises tegobuvir.

Other formulation approaches, such as liquid-based formulations, simple solutions, nanoparticles, crystalline solids, salts or co-crystals, and conventional immediate release formulations, can also be employed to formulate the selected HCV inhibitors, either alone or in combination with other anti-HCV agents.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A solid oral dosage form comprising a solid solution which includes:

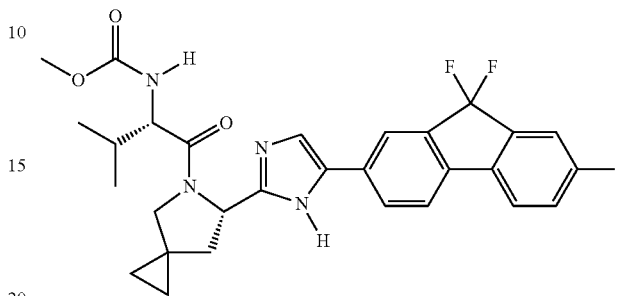

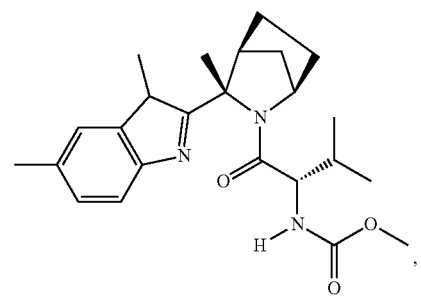

copovidone, and optionally a pharmaceutically acceptable surfactant.

2. The solid dosage form of claim 1, which is a tablet.

3. The solid dosage form of claim 2, wherein said tablet is film coated.

4. The solid dosage form of claim 1, which further comprises another anti-HCV agent.

5. A method of treating HCV infection, comprising administering the solid oral dosage form of claim 1 to a patient in need thereof.

* * * * *